United States Patent [19]

Gonick et al.

[11] Patent Number: 5,667,811
[45] Date of Patent: Sep. 16, 1997

[54] NA-K-ATPASE INHIBITING NATRIURETIC SUBSTANCES

[75] Inventors: Harvey C. Gonick, Los Angeles; Elmar Weiler, Inglewood; Farhad Khalil-Manesh, Los Angeles, all of Calif.

[73] Assignee: The Regents of the University of California, Oakland, Calif.

[21] Appl. No.: 983,617

[22] Filed: Nov. 30, 1992

Related U.S. Application Data

[63] Continuation of Ser. No. 581,582, Sep. 11, 1990, abandoned.
[51] Int. Cl.$^6$ .................. A61K 35/16; A61K 35/14
[52] U.S. Cl. .................. 424/530; 424/529; 424/531
[58] Field of Search .................. 424/536, 531, 424/545, 530; 530/830, 834

[56] References Cited

U.S. PATENT DOCUMENTS

| | | | |
|---|---|---|---|
| 4,321,120 | 3/1982 | Nardi et al. | |
| 4,665,019 | 5/1987 | Hamlyn et al. | 435/21 |
| 4,727,061 | 2/1988 | Kramer et al. | 514/18 |
| 4,746,652 | 5/1988 | Buckalew, Jr. et al. | 514/77 |
| 4,780,314 | 10/1988 | Graves | 424/545 |
| 4,780,410 | 10/1988 | Matsuda et al. | 435/7 |
| 4,782,014 | 11/1988 | Serban et al. | 435/7 |
| 4,940,670 | 7/1990 | Rhodes | 436/548 |
| 4,940,782 | 7/1990 | Rup et al. | 530/387 |
| 4,943,533 | 7/1990 | Mendelsohn et al. | 435/240.27 |

FOREIGN PATENT DOCUMENTS

2597483  10/1987  France.

OTHER PUBLICATIONS

Morgan et al. (1985) J. Biol. Chem. 260(25):13595–13600.
Cloix et al. (1984) Experientia 40:1380–1382.
Hamlyn et al. (1989 Jun.) Hypertension 13 (6 pt.2): 681–689 (abstract only).
Weber et al. (1989, Oct.) Am. J. Hypertens. 2(10):754–61 (abstract only).
Gruber et al. (1978) Proc. Soc. Exp. Biol. Med. 159:463–467.
Haupert et al. (1984, Dec.) Am. J. Physiol. (6 Pt2) 247 F919–F924.
Gonick et al. (CV).
Gonick et al. (CH).
Veress et al. (1980) Clin. Su: 59:183–189.
Devynck et al. (1984) J. Physiol. 79:538–541.
Hamlyn et al. (1989, Jun.) Hypertension 13(6 Pt. 3):681–689. (abstract only).
Weber et al. (1989, Oct.) Am. J. Hypertens. 2(10):754–761. (abstract only).
Garner et al. (1984) Am. J. Physiol. 247(6 Pt. 2):F919–F924.
Kelly et al. (1985) J. Biol. Chem. 260(21):11396–11405.
Crabos et al. (1984) FEBS Lett. 176(1):223–228.
Roberts & Maurer, "Blood Pressure Levels of Persons 6–74 years", *Vital health Stat* 203:1 (1977).

Krishan, "Hypertension: Definition, Prevalence and Prognosis", in Spittel, Clinical Medicine, Harper & Row, Philadelphia, P.A. (1986).
Dahl, "Salt and Hypertension", *Am. J. Clin. Nutr.*, 25:231 (1972).
Blaustein, "Role of a Natriuretic Factor in Essential Hypertension: An Hypothesis", *Ann, Int. Med.* 898:785–792 (1983).
Weber, et al., "Effects of a Human–Derived Sodium Transport Inhibitor on in vitro Vascular Reactivity", *Am. J. Hypertension*, 2(10):754–761 (1989).
Chiba, et al., "Vasoconstrictor Effects of Endogenous Digitalis–Like Factors Extracted from Urine of Hypertensive Patients", *Heart Vessels*, 3(3):129–134 (1987).
Mir, et al., "Calcium Retention and Increased Vascular Reactivity Caused by a Hypothalamic Sodium Transport Inhibitor", *Clin. Sci.*, 75:197–202 (1988).
Haupert, "Regulation of $Na^+$–$K^+$–ATPase by the Endogenous Sodium Transport Inhibitor form Hypothalamus", *Hypert*, (Suppl. I) 10:I61–I66 (1987).
Buckalew and Nelson, "Natriuretic and Sodium Transport Inhibitory Activity in Plasma of Volume–Expanded Dogs", *Kidney Int.*, 5:12–22 (1974).
Gonick, et al., "Circulating Inhibitor of Sodium–Potassium–Activated Adenosine Triphosphatase after Expansion of Extracellular Fluid Volume in Rats", *Clin. Sci.*, 53:329–334 (1977).
Gonick, et al., "Regulation of Extracellular Volume: Critical Evaluation of Natriuretic Hormones", In Kruck & Thurau, Eds., Endocrine Regulation of Electrolyte Balance, Springer, Berlin, Heidelberg, New York, Tokyo, pp. 104–120.
Raghavan & Gonick, "Partial Purification and Characterization of Natriuretic Factor from Rat Kidney", *Proc. Soc. Exp. Biol. Med.*, 164(1):101–104 (1980).
Gonick & Saldanha, "A Natriuretic Principle Derived from Kidney Tissue of Volume Expanded Rats", *J. Clin. Invest.*, 56:247–255 (1975).
DeBold, "Heart Atria Granularity Effects of Changes in Water–Electrolyte Balance", *Proc. Soc. Exp. Med. Biol.*, 161:508–511 (1979).
Atlas, et al., "Purification, Sequencing and Synthesis of Natriuretic Vasoactive Rat Atrial Peptide", *Nature*, 309:717–722 (1984).

(List continued on next page.)

*Primary Examiner*—Avis M. Davenport
*Attorney, Agent, or Firm*—Merchant, Gould, Smith, Edell, Welter & Schmidt

[57] ABSTRACT

The invention provides methods for obtaining substantially purified high and low molecular weight Na-K-ATPase inhibitor compounds having natriuretic and vasoconstrictive activity, antibodies reactive with the compounds and methods for their use in diagnostic and therapeutic applications to detect elevated or decreased amounts of the compounds in subjects having diseases associated with the presence or deficiency of these natriuretic compounds.

1 Claim, 16 Drawing Sheets

OTHER PUBLICATIONS

Cogan, "Atrial Natriuretic Factor Can Increase Renal Solute Excretion Primarily by Raising Glomerular Filtration", *Am. J. Physiol.*, 250:F710–714 (1986).

Soejima, et al., "Renal Response of Anesthetized Rats to Low–Dose infusion of Atrial Natriuretic Peptide", *Am. J. Physiol.*, 255:R449–R455 (1988).

Flynn, et al., "The Amino Acid Sequence of an Atrial Peptide with Potent Diuretic and Natriuretic Properties", *Biochem. Biophys. Res. Commun.* 117:859–865 (1983).

Burgisser, et al., "Human Cardiac Plasma Concentrations of Atrial Natriuretic Peptide Quantified by Radioreceptor Assay", *Biochem. Biophys. Res. Comm.*, 133:1201–1209 (1985).

Raine, et al., "Atrial Natriuretic Peptide and Atrial Pressure in Patients with Congestive Heart Failure", *New Eng. J. Med.* 315:534–537 (1986).

Gruber & Buckalew, "Further Characterization and Evidence for a Precursor in the Formation of Plasma Antinatriferic Factor", *Proc. Soc. Exp. Biol. Med.* 159:463–467 (1978).

Hamlyn, et al. "A Circulating Inhibitor of ($Na^+ + K^+$ ATPase) Associated with Essential Hypertension", *Nature*, 300:650–652 (1982).

Kelly, et al., "Characterization of Digitalis–Like Factors in Human Plasma. Interactions with Na–K–ATPase and Cross–Reactivity with Cardiac Glycoside–Specific Antibodies", *J. Biol. Chem.* 260:11396–11405 (1985).

Devynck et al., "Measurement of Digitalis–Like Compound in Plasma: Application in Studies of Essential Hypertension", *Br. Med. J.*, 287:631–634 (1983).

Weiler, et al., "Observations on the Cascade" of Na–K–ATPase Inhibitory and Digoxin–Like–Immunoreactive Material in Human Urine: Possible Relevance to Essential Hypertension, *Clin. Exp. Hypertension* (A)7 & (5 and 6):809–836 (1985).

Kramer, et al., "Further Characterization of the Endogenous Natriuretic and Digoxin–Like Immunoreactivity Activities in Human Urine: Effect of Changes in Sodium Intake" *Renal Physiol.*, 8:80–89 (1985).

Crabos, et al., "Measurement of Endogenous $Na^+$, $K^+$–ATPase Inhibitors in Human Plasma and Urine Using High–Performance Liquid Chromatography", FEBS Letters, 176:223–228 (1984).

Klingmulter, et al., "Digoxin–Like Natriuretic Activity in the Urine of Salt Loaded Healthy Subjects", *Klin. Wochenschr.*, 60(19)1249–1253 (1982).

Kelly, et al., "Identification of NaK–ATPAse Inhibitors in Human Plasma as Nonesterfied Fatty Acids and Lysophospholipids", *J. Biol. Chem.* 261:11704–11711 (1986).

Cloix, et al., "High–Yield Purification of a Urinary $Na^+$–Pump Inhibitor", *Biochem. Biophys. Res. Commun.*, 131:1240 (1985).

Gruber, et al., "Further Characterization and Evidence for a Precursor in the Formation of Plasma Antinatriferic Factor" *Proc. Soc. Exp. Biol. Med.*, 159:463–467 (1978).

Gruber, et al., "Endogenous Digitalis–Like Subtance in Plasma of Volume–Expanded Dogs", *Nature*, 287:743–745 (1980).

Sealey, et al., "Natriuretic Activity in Plasma and Urine of Salt–Loaded Man and Sheep", *J. Clin. Invest.*, 48:221–224 (1969).

Clarkson, et al., "Two Natriuretic Substances in Extracts of Urine from Normal Man When Salt–Depleted and Salt–Loaded", *Kidney Int.*, 10:381–394 (1976).

Morich & Garthoff, "Characteristic Changes of Plasma Proteins in the Dahl Hypertensive Rat Strain (DS) During the Development of Hypertension" *Hypertension*, 3:1249–1253 (1985).

John, et al., "Identification of a So–Far Not Characterized Human Serum Protein Associated with Essential Hypertension", *Electrophoresis*, 6:292–295 (1985).

Cloix, et al., "Plasma Protein Changes in Primary Hypertension in Humans and Rats", *Hypertension*, 5:128–134 (1983).

Van de Voorde, et al., "Isolation of a Plasma Protein Observed in Patients with Essential Hypertension", *Biochem. Biophys. Res.*, 111:1015 (1983).

Weiler, et al., "Circulating High Molecular Weight Form of No–K–ATPase Inhibitor: Changes in Disease", *Clin. Res.*, 34:90A (1986).

Veress, et al., "Characterization of the Natriuretic Activity in the Plasma of Hypervolaemic Rats", *Clin. Sci.*, 59:183–189 (1980).

Pearce & Veress, "Concentration and Bioassay of a Natriuretic Factor in Plasma of Volume Expanded Rats", *Can. J. Physiol. Pharmacol.*, 53:742–747 (1975).

Gruber, et al., "Evidence that Natriuretic Hormone is a Cascading Peptide Hormone System", In Lichardus, et al., Eds. Hormonal Regulation of Sodium Excretion, Elsevier/North–Holland, Amsterdam, pp. 349–355 (1980).

Gonick, et al., "Pattern of Na–K–ATPase Inhibitors in Plasma and Urine of Hypertensive Patients: A Preliminary Report", *Klin. Wochenschr.* 65 (Suppl. VIII); 139:145 (1987).

Devynck, et al., "Clinical and Biochemical Approach of a Circulating $Na^+$–Pump Inhibitor", *J. Physiol.*, 79:538–541 (1984).

Huot, et al., "Sodium–Potassium Pump Activity in Reduced Renal Mass Hypertension", *Hypertension*, 5:94–100 (1983).

MacGregor, et al., "Evidence for a Raised Concentration of a Circulating Sodium Transport Inhibitor in Essential Hypertension", *Br. Ned. J.*, 283:1355–1365 (1981).

Edmondson & MacGregor, "Leucocyte Cation Transport in Essential Hypertension: Its Relationship to the Renin–Angiotensin System", *Br. Med. J.*, 282:12671269 (1981).

Haddy, et al., "Humoral Factors and the Sodium–Potassium Pump in Volume–Expanded Hypertension", *Life Sci.*, 24:2105–2118 (1979).

Blaustein, "Sodium Ions, Calcium Ions, Blood Pressure Regulation and Hypertension: A Reassessment and a Hypothesis", *Am. J. Physiol.*, 232:C165–C173 (1977).

De Wardener & MacGregor, "The Relation of a Circulating Transport Inhibitor (the Natriuretic Hormone?) to Hypertension", *Medicine*, 62:310–326 (1983).

Bourgoignie, et al., "The Presence of a Natriuretic Factor in Urine of Patients with Chronic Uremia. The Absence of the Factor in Nephrotic Uremic Patients", *J. Clin. Invest.*, 53:1559–1567 (1974).

Boero, et al., "Erythrocyte Na,K Pump Activity & Arterial Hypertension in Uremic Dialyzed Patients", *Kidney Int.*, 34:691–695 (1988).

Kelly, et al., "Endogenous Digitalis–Like Factors in Hypertension and Chronic Renal Insufficiency", *Kidney Int.*, 30:723–729 (1986).

Devynck, et al., "Circulating Inhibitor of Sodium Active Transport in Essential Hypertension and Volemic Expansion", translation of abstract only *Arch. Maj. Coeur,* 78:1691–1695 (1985).

Krzesinski, et al., "Arguments for the Presence of a Na–K ATPase Inhibitor in the Plasma of Uremic and Essential Hypertensive Patients", *Clin. Exp. Physiol.,* 79:538–541 (1984).

Tikkanen, et al., "Plasma Atrial Natriuretic Peptide in Cardiac Disease and During infusion in Healthy Volunteers", *Lancet,* 2:66 (1985).

Gonick, et al., "High and Low Molecular Weight Plasma Na–K–ATPase Inhibitors (NKAI) in Hypertension", presented at post–congress Satellite Symposium on Natriuretic Hormones in Hypertension, following the Xth International Congress of Nephrology, London, England, Aug. (1987).

Weiler, et al., "High Molecular Weight (HMW) Plasma Na–K–ATPase Inhibitor (NKAI) in Essential Hypertension (EH)", abstract, Proceedings of the Third Annual Meeting of The American Society of Hypertension in New York, Jun. 1988 (*Amer. J. Hypertension* 1(3) Part 2:47A (1988).

Kruck and Kramer, "Third Factor and Edema Formation", *Contr. Nephrol.* 13:12–20 (1987).

Kramer and Kruck, "Plasma Natriuretic Activity in Oedematous States", *Proc, Eur. Dial. Transplant. Ass.* 12:321–329 (1976).

Rivier, et al. "Reversed–Phase High–Performance Liquid Chromatography of Insulins from Different Species", *J. Chromatog.,* 268:112–119 (1983).

Rivier, et al. "Reversed–Phase High–Performance Liquid Chromatography of Insulins from Different Species", *J. Chromatog.,* 288:303–328 (1984).

Laemmli, "Cleavage of Structural Proteins During the Assembly of the Head of Bacteriophage T4", *Nature,* 277:680–685 (1970).

Fallon, et al., "Laboratory Techniques in Biochemistry and Molecular Biology", vol. 17, Chapters 3 and 11, pp. 23–42 and 260–270 (1987).

Tamura, et al., "Isolation and Characterization of a Specific Endogeous $Na^+,K^+$–ATPase Inhibitor from Bovine Adrenal", *Biochem.,* 27:4244–4253 (1988).

Fisk & Subbarow, "Colorimetric Determination of Phosphorous", *J. Biol. Chem,* 66:375:381 (1925).

Mullis & Faloona, "Specific Synthesis of DNA in Vitro Via A Polymerase–Catatyzed Chain Reaction", *Methods Enzymol.* 155:335–350 (1987).

Kohler & Milstein, "Continuous Cultures of Fused Cells Secreting Antibody of Predefined Specificity", *Nature,* 256:495–497 (1975).

Young & Davis, "Yeast RNA Polymerase II Genes: Isolation with Antibody Probes", *Science,* 222:728 (1983).

Sanger, et al., "DNA Sequencing with Chain–Terminating Inhibitors", *Proc. Natl. Acad. Sci. USA,* 74:5463 , (1977).

Messing, et al., "A System for Shotgun DNA Sequencing", *Nucleic Acids Res.,* 9:309 (1981).

Maxam, "Sequencing End–Labeled DNA with Base-Specific Chemical Cleavages", *Methods in Enzymol.,* 65:499 (1980).

Uotila, et al., "Two–Site Sandwich Enzyme Immunoassay with Monoclonal Antibodies to Human AFP":, *J. Immunol. Methods,* 42:11 (1981).

Sikora, et al., (eds) "Biochemistry", *Monoclonal Antibodies,* pp. 32–52, Blackwell Scientific Publications (1984).

Hamlyn, et al., "Isolation and Characterization of a Sodium Pump Inhibitor From Human Plasma", *Hypertension,* 13(6):681–689, Jun., 1989.

Haupert, et al., Hypothalamic Sodium–Transport Inhibitor is a High–Affinity Reversible Inhibitor of $Na^+$–$K^+$–ATPase, *Am. J. Physiol.,* 247(6 pg. 2) F919–F924 (1984).

Pamnani, et al. "Effects of Three Sodium–Potassium Adenosine Triphosphatase Inhibitors", *Hypertension* 18(3):316–324 (1991).

Hamlyn, et al., abstract "Identification and Characterization of a Ouabain–Like Compound from Human Plasma", (published erratum appears in *Proc. Natl. Acad. Sci. USA,* 88(21):9907 (1991).

Matthews, et al., "Mass Spectral Characterization of an Endogenous Digitalislike Factor for Human Plasma", *Hypertension,* 17(6):930–935 (1991).

Cloix, et al., "Purification from Human Plasma of Endogenous Sodium Transport Inhibitor(s)"*Experientia,* vol. 40, issued 1984, pp. 1380–1382.

NA-K-ATPASE INHIBITING NATRIURETIC SUBSTANCES

This is a continuation of copending application Ser. No. 07/581,582 filed on Sep. 11, 1990 and now abandoned.

FIELD OF THE INVENTION

The present invention relates to the identification, isolation and purification of Na-K-ATPase inhibiting substances having natriuretic properties, more particularly to low molecular weight hypothalamic-renal natriuretic substances associated with hypertension and congestive heart failure, and to methods of using the substances to diagnose and treat disease.

BACKGROUND OF THE INVENTION

Blood pressure is a function of the total volume of blood and the resistance to its flow through the circulatory system, which in turn is determined by the degree of constriction of small blood vessels called arterioles. Hypertension, characterized by an abnormally high arterial blood pressure relative to normal blood pressure (below 140 mm Hg systolic, 90 mm Hg diastolic), is a frequent and dangerous pathological condition that affects a large number of people throughout the world. The prevalence of hypertension may be as high as 60 million adults in the United States alone. Unfortunately, the disease remains undetected in large segments of the population. Low-renin hypertension, which constitutes about one-quarter of the total cases of hypertension in man, is characterized by expanded blood volumes and low concentrations of renin, a protein-digesting enzyme released by the kidney that initiates the production of angiotensin, a potent constrictor of blood vessels.

The prevalence of definite hypertension (systolic blood pressure greater than 160 mm Hg and diastolic pressure greater than 95 mm Hg) is 18.1 per 100 adults in the age group of 18 to 74 years (Roberts and Maurer, "Blood Pressure Levels of Persons 6–74 years, United States, 1971–1974", *Vital Health Stat.* 203:1 (1977)). Borderline hypertension, defined as blood pressure above 140 mm Hg systolic and 90 mm Hg diastolic, but less than 159 mm systolic and 94 mm diastolic, has been found in approximately 25 million persons (Krishan, "Hypertension: Definition, Prevalence and Prognosis", in Spittell, "Clinical Medicine", Harper and Row, Philadelphia, Pa., (1986)). Hypertension is a leading contributor to cardiovascular disability including stroke, congestive heart failure (CHF) and coronary artery disease, sometimes resulting in premature death. There are a few well-defined causes of hypertension, including kidney disease, narrowing of kidney arteries ("renovascular hypertension") and certain endocrine conditions associated with high circulating hormone levels, e.g. pheochromocytoma (due to excessive epinephrine and/or norepinephrine levels) and aldosteronoma (due to excessive aldosterone levels).

The presence of excess amounts of sodium chloride, i.e. "salt", has long been implicated in the pathogenesis of hypertension (see Dahl, "Salt and hypertension", *Am. J. Clin. Nutr.* 25:231 (1972)). Increased amounts of sodium are thought to result in excess fluid volume that interferes with normal physiology. In addition, it has been suggested that potassium may modulate the effects of sodium in the development of hypertension. Recent evidence suggests that hormones may be the link between excessive dietary salt intake and at least some forms of hypertension. These hormones, called "natriuretic" (salt-losing) hormones are thought to act on sodium ion transport first on the kidneys, increasing the excretion of sodium ions into the urine, and, secondly, on other cells of the body. Sodium ion transport is performed by a "pump" utilizing the energy released during the hydrolysis of adenosine triphosphate (ATP) by the enzyme sodium, potassium activated adenosine triphosphatase (Na-K-ATPase, E.C. 3.6.1.3). The hypothalamic-renal form of natriuretic hormones are thought to inhibit this enzyme, i.e. act as circulating sodium pump transport inhibitors.

One theory suggests that hypertension results from the effect of the circulating sodium pump transport inhibitors on vascular endothelial transport of sodium and calcium, resulting in retention of calcium within the vascular endothelial cell, and hence enhanced vascular contractility (Blaustein, "Role of a natriuretic factor in essential hypertension: An hypothesis" *Ann. Int. Med.* 898:785–792 (1983)). A later study showed that low molecular weight inhibitors (<1K daltons) in urine induce or potentiate vasoconstriction in isolated rabbit blood vessels (Weber et al., "Effects of a human-derived sodium transport inhibitor on in vitro vascular reactivity" *J. Hypertension* 2(10):754–761 (1989)). One of the low molecular weight substances was observed to be more potent than the other urine fraction in inducing spontaneous vasoconstriction and in potentiating vasoconstriction caused by norepinephrine or angiotensin. Use of calcium channel blockers or low calcium bath suggested that the inhibitors exert their effect, at least in part, via control of calcium ion movement in vascular smooth muscle cells. Other researchers have shown similar vasoconstrictive effects of endogenous sodium transport inhibitors (Chiba et al., "Vasoconstrictor effects of endogenous digitalis-like factors extracted from urine of hypertensive patients", *Heart Vessels* 3(3):129–134 (1987); and Mir et al., "Calcium retention and increased vascular reactivity caused by a hypothalamic sodium transport inhibitor", *Clin. Sci.* 75: 197–202 (1988)). Thus, natriuretic substances may cause smooth muscle cells in arterioles to contract, raising blood pressure.

Studies in man and animals with experimentally expanded blood volumes have also confirmed that many cases of hypertension are associated with an increased circulating plasma level of one or more sodium transport inhibitors. Increased amounts of natriuretic substances have also been detected in acutely volume-expanded subjects. It has been suggested that volume expansion triggers the brain to initiate the production or secretion of natriuretic substances. Two major volume-responsive natriuretic hormone systems are believed to exist. The first system alluded to above involves a hormone most likely synthesized in the posterior hypothalamus ("hypothalamic-renal natriuretic hormone") (Haupert, "Regulation of Na-K-ATPase by the endogenous inhibitor from hypothalamus", *Hypert.* (Suppl. I) 10:161–166 (1987)), which acts as a transport inhibitor in anuran membrane systems (Buckalew and Nelson, "Natriuretic and sodium transport inhibitory activity in plasma of volume-expanded dogs", *Kidney Int.* 5:12–22 (1974)), inhibits Na-K-ATPase (Gonick et al., "Circulating inhibitor of sodium-potassium-activated adenosine triphosphatase after expansion of extracellular fluid volume in rats", *Clin. Sci.* 53:329–334 (1977); Gonick et al., "Regulation of Extracellular Volume: Critical evaluation of natriuretic hormones", In Kruck and Thurau, Eds., Endocrine Regulation of Electrolyte Balance, Springer, Berlin, Heidelberg, New York, Tokyo, pp. 104–120 (1986); and Raghavan and Gonick, "Partial purification and characterization of natriuretic factor from rat kidney", *Proc. Soc. Exp. Biol. Med.*

164(1):101–104 (1980)) and causes a natriuresis (increased sodium excretion into the urine), without attendant kaliuresis (increase in potassium excretion in the urine) or change in renal hemodynamics when injected into test animals (Gonick and Saldanha, "A natriuretic principle derived from kidney tissue of volume expanded rats", *J. Clin. Invest.* 56:247–255 (1975)).

The second natriuretic hormone, referred to as "atrial natriuretic factor" ("ANF") or "atrial natriuretic peptide" ("ANP") is either synthesized or stored in cardiac atria (deBold "Heart atria granularity effects of changes in water-electrolyte balance", *Proc. Soc. Exp. Med. Biol.* 161:508–511 (1979)) and does not inhibit active transport (Atlas et al., "Purification, sequencing and synthesis of natriuretic vasoactive rat atrial peptide", *Nature* 309:717–722 (1984)). At high blood levels, ANF exerts its predominant natriuretic effect via increasing renal glomerular filtration rate (Cogan, "Atrial natriuretic factor can increase renal solute excretion primarily by raising glomerular filtration", *Am. J. Physiol.* 250:F710–714 (1986)), while at lower blood levels, natriuresis occurs via a direct effect on tubular transport of sodium, without alteration in glomerular filtration rate (Soejima et al., "Renal response of anesthetized rats to low-dose infusion of atrial natriuretic peptide", *Am. J. Physiol.* 255:R449–R455 (1988)). ANF has been structurally identified (Flynn et al., "The amino acid sequence of an atrial peptide with potent diuretic and natriuretic properties", *Biochem. Biophys. Res. Commun.* 117:859–865 (1983)) and a radioimmunoassay has been developed (Burgisser et al., "Human cardiac plasma concentrations of atrial natriuretic peptide quantified by radioreceptor assay", *Biochem. Biophys. Res. Comm.* 133:1201–1209 (1985)). In congestive heart failure, ANF levels have been shown to be increased above normal, reflecting release secondary to dilatation of the cardiac atria (Raine et al., "Atrial natriuretic peptide and atrial pressure in patients with congestive heart failure", *New Eng. J. Med.* 315:534–537 (1986)). This increase in ANF is physiologically ineffective or only partially effective, as demonstrated by the persistence of the avid renal sodium reabsorption characteristic of congestive heart failure.

In contrast to the more recently discovered ANF, the hypothalamic-renal natriuretic hormone (HRNH) has not been purified sufficiently to provide structural information or to permit the development of a radioimmunoassay. Thus, studies of changes in the circulating level of HRNH following physiological manipulations or in human disease states have relied on the use of certain functional properties tested in biological assays; on size (i.e. molecular weight) and conditions under which the hormone is detected to identify and quantify the changes. Natriuretic activity is typically assayed by injecting the putative natriuretic substance into a test animal such as a rat and determining whether sodium excretion into the urine increases in response to the administered substance. In addition to the production of natriuresis in a bioassay animal, the transport inhibitor has been identified by a variety of techniques including: 1) inhibition of short circuit current in anuran membranes ("antinatriferic" activity) (Gruber and Buckalew, "Further characterization and evidence for a precursor in the formation of plasma antinatriferic factor", *Proc. Soc. Exp. Biol. Med.* 159:463–467 (1978)); 2) direct inhibition of purified Na-K-ATPase ATPase (Hamlyn et al., "A circulating inhibitor of $Na^+$ associated with essential hypertension", *Nature* 300:650–652 (1982)); 3) displacement of tritiated ouabain from receptors on purified Na-K-ATPase (Kelly et al., "Characterization of digitalis-like factors in human plasma. Interactions with Na-K-ATPase and cross-reactivity with cardiac glycoside-specific antibodies", *J. Biol. Chem.* 260:11396–11405 (1985)) or red cell membrane Na-K-ATPase (Devynck et al., "Measurement of digitalis-like compound in plasma: application in studies of essential hypertension" *Br. Med. J.* 287:631–634 (1983)); 4) inhibition of active transport in isolated membranes (Buckalew and Nelson, supra), or cells (Edmonson et al.; Haddy et al., De Wardener and MacGregor; Blaustein and Kelly et al., supra); and 5) cross-reactivity with digoxin antibodies (Kelly et al., supra). This last technique may be the least discriminating because significant discrepancies have been observed in serum or urine fractions which show enhanced Na-K-ATPase inhibitory activity or natriuretic activity but not digoxin immunoreactivity, or the reverse (Kelly et al., supra; Weiler et al., "Observations on the "cascade" of Na-K-ATPase inhibitory and digoxin-like immunoreactive material in human urine: Possible relevance to essential hypertension", *Clin. Exp. Hypertension* [A]7 (5 and 6):809–836 (1985); Kramer et al., "Further characterization of the endogenous natriuretic and digoxin-like immunoreactivity activities in human urine:effect of changes in sodium intake", *Renal Physiol.* 8:80–89 (1985) and Crabos et al., "Measurement of endogenous $Na^+$, $K^+$-ATPase inhibitors in human plasma and urine using high-performance liquid chromatography", *FEBS Letters* 176:223–228 (1984); Klingmuller et al., "Digoxin-like natriuretic activity in the urine of salt loaded healthy subjects", *Klin. Wochenschr.* 60(19)1249–1253 (1982)).

In at least one study which reported an increased level of Na-K-ATPase inhibitory activity in urine fractions of hypertensives as compared to normals, no parallel changes were found in digoxin immunoreactivity (Weiler et al., supra). On the other hand, several non-humoral agents in plasma have been found to be potent Na-K-ATPase inhibitors, including non-esterified fatty acids and lysophosphatidyl choline (Kelly et al., "Identification of Na, K-ATPase inhibitors in human plasma as nonesterified fatty acids and lysophospholipids",*J. Biol. Chem.* 261:11704–11711 (1986) ). Thus, great care must be taken to evaluate plasma inhibitors of Na-K-ATPase to exclude all non-specific inhibitors.

Attempts to purify NH materials have resulted in putative NH compounds having one or more of the above-enumerated activities and of varying molecular weights. When Na-K-ATPase inhibitory activity is used to bioassay NH, several low molecular weight forms have been detected in deproteinized plasma following separation by HPLC. One study reports three low molecular weight fractions in desalted, deproteinized human plasma, separated by HPLC, which displayed Na-K-ATPase inhibitory activity, inhibited sodium pump activity in erythrocytes, displaced $^3$H-ouabain from canine kidney Na-K-ATPase, and cross-reacted with polyclonal and monoclonal digoxin-specific antibodies (Kelly et al., 1985, supra). A fourth fraction cross-reacted with digoxin antibodies, but was not an Na-K-ATPase inhibitor.

Crabos et al., supra, also sought endogenous Na-K-ATPase inhibitors in HPLC-separated, deproteinized plasma and urine from hypertensive and normotensive urines. Three Na-K-ATPase inhibitors were found in plasma and two inhibitors in urine. Of the plasma fractions, two showed equal potency in a digoxin radioimmunoassay, while one showed minimal cross-reactivity with digoxin antibody. Two of the inhibitors were also present to a greater degree in plasma of hypertensive patients than in plasma from normotensive controls. A fourth plasma fraction reacted with digoxin antibodies, but did not inhibit Na-K-ATPase. Cloix et al., ("High-yield purification of a urinary Na pump inhibitor", *Biochem. Biophys. Res. Commun.* 131:1234–1240 (1985)) have reported purification to homogeneity of a low molecular weight Na-K-ATPase inhibitor from human urine. This compound appears to be a glycosteroid with molecular weight less than 500 daltons. Gruber et al. described two low molecular weight Na-K-ATPase inhibitors in plasma of volume expanded dogs that also cross-react with digoxin antibody (Gruber et al., "Further characterization and evidence for a precursor in the formation of plasma antinatriferic factor", *Proc. Soc. Exp. Biol. Med.* 159:463–467 (1978) and Gruber et al., "Endogenous, digitalis-like substance in plasma of volume-expanded dogs", *Nature* 287:743–745 (1980)).

In general, these putative NH materials have molecular weights of less than 1000 and some show cross-reactivity with digoxin antibodies. Less attention has been focused on high molecular weight compounds (10,000 to 50,000 daltons) from plasma or urine, which have the properties of inducing natriuresis or inhibiting the Na-K-ATPase pump. These compounds have not been well characterized physiologically or biochemically.

Sealey et al., ("Natriuretic activity in plasma and urine of salt-loaded man and sheep", *J. Clin. Invest.* 48:221–224 (1969)) first described the presence of a high molecular weight natriuretic compound in urine and deproteinized plasma from salt-loaded man and sheep. Clarkson et al. ("Two natriuretic substances in extracts of urine from normal man when salt-depleted and salt-loaded", *Kidney Int.* 10:381–394 (1976)) reported that both high and low molecular weight natriuretic compounds could be recovered from urine of salt-loaded man. The high molecular weight compound characteristically had a delayed onset of action and produced a relatively long duration of natriuresis, while the low molecular weight compound had an immediate onset and shorter duration of action.

High molecular weight proteins have also been demonstrated in plasma from hypertensive animals and humans. Researchers have described a 14 to 15 kD protein band in plasma of Dahl salt-sensitive rats, which increased in intensity as hypertension developed with salt loading, but was much less affected by salt loading in Dahl salt-resistant rats (Morich and Garthoff ("Characteristic changes of plasma proteins in the Dahl hypertensive rat strain (DS) during the development of hypertension", *Hypertension* 3:1249–253 (1985)). Additional work characterized this "hypertension associated protein" as having a molecular weight of approximately 15,500 daltons and as the alpha 1-chain of haptoglobin (John et al., "Identification of a so-far not characterized human serum protein associated with essential hypertension", *Electrophoresis* 6:292–295 (1985)). Cloix et al., ("Plasma protein changes in primary hypertension in humans and rats" *Hypertension* 5:128–134 (1983)), found a similarly sized protein (molecular weight 13,000 daltons) in plasma from hypertensives (87%) as contrasted to 26% of normotensives without history of hypertension. Van de Voorde et al., "Isolation of a plasma protein observed in patients with essential hypertension", *Biochem. Biophys. Res.* 111:1015 (1983), found a 105 kD protein in plasma of essential hypertensives that could be broken down to two 45 kD and one 15 kD components.

In recent studies, Weiler et al., "Circulating High Molecular Weight Form of Na-K-ATPase Inhibitor: Changes in Disease", *Clin. Res.* 34:90A (1986) isolated a protein band of molecular weight of approximately 10,000 daltons in plasma and compared the presence of the band in plasma from patients with primary aldosteronism, chronic renal failure, congestive heart failure and normals. The results demonstrated increased intensity of staining of the band in primary aldosteronism and chronic renal failure, and decreased intensity of the band in congestive heart failure, indicating that the amount of the protein varied in proportion to "effective circulating blood volume" in disease states.

The majority of the prior investigations of the circulating transport inhibitor(s) in hypertension have employed whole plasma or plasma extracts as the source of the inhibitor(s). However, there is evidence that the circulating substance, measured either as a natriuretic compound, or as a Na-K-ATPase inhibitor, exists in several forms both in plasma and urine, including a carrier-bound moiety (Veress et al., "Characterization of the natriuretic activity in the plasma of hypervolaemic rats", *Clin. Sci.* 59:183–189 (1980); Pearce and Veress, "Concentration and bioassay of a natriuretic factor in plasma of volume expanded rats", *Can. J. Physiol. Pharmacol.* 53:742–747 (1975); and Weiler et al., "Observations on the "Cascade" of Na-K-ATPase Inhibitory and Digoxin-Like Immunoreactive Material in Human Urine: Possible Relevance to Essential Hypertension", *Clin. and Exper Theory and Practice A7*(5 & 6):809–836 (1985)), and one or more precursors (Gonick et al., Endocrine Regulation of Electrolyte Balance, supra; and Gruber et al., "Evidence that natriuretic hormone is a cascading peptide hormone system", In Lichardus et al., Eds., Hormonal Regulation of Sodium Excretion, Elsevier/North-Holland, Amsterdam, pp. 349–355 (1980)).

Veress and co-workers ("Characterization of the natriuretic activity in the plasma of hypervolaemic rats", *Clin. Sci.* 59:183–189 (1980)) have demonstrated that when plasma is not deproteinized and is separated on Sephadex with an eluate of low ionic strength, the natriuretic activity is confined to a large protein fraction (molecular weight >30K daltons), whereas separation with an eluate of high ionic strength yields both high and low molecular weight natriuretic factors. These researchers concluded that natriuretic factor may occur in plasma in both protein-bound and free forms and that deproteinization of plasma or use of a high ionic strength buffer might separate the low molecular weight form from its carrier protein.

In additional studies by Gruber et al., these researchers suggested that the quantity of the final low molecular weight NH present in plasma was a function of the method of processing the plasma sample. Rapid processing of chilled blood collected in the presence of an enzyme inhibitor, bacitracin, with subsequent acidification and boiling, yielded predominantly a "precursor" low molecular weight NH, while plasma processed slowly, without bacitracin, and incubated at room temperature for 30 minutes yielded a "final" low molecular weight NH. These observations provided a hypothesis that a precursor, low molecular weight NH was metabolized to a final low molecular weight NH by proteolytic enzymes and was the major circulating form of the low molecular weight NH.

Thus, in contrast to the majority of previous studies in which plasma is deproteinized by heating and/or acidification prior to assay, these studies suggest that initial deproteinization must be avoided if the presence of high molecular weight natriuretic substances or pump inhibitors are to be sought.

In a study comparing both plasma and urine in normotensives and hypertensives (Gonick et al., "Pattern of Na-K-ATPase inhibitors in plasma and urine of hypertensive patients: A preliminary report", *Klin. Wochenschr.* 65 (Suppl. VIII):139–145 (1987)), sequential Amicon® filtration was performed, followed by Sep-Pak° HPLC separation of the low molecular weight (less than 1 kD) fractions. These studies confirmed that hypertensive urine contained increased quantities of a high molecular weight (30 kD to 50 kD) Na-K-ATPase inhibitor and one low molecular weight inhibitor. In plasma (collected in chilled tubes containing proteolytic enzyme inhibitors to avoid denaturation), two low molecular weight plasma inhibitors were increased, but relatively little Na-K-ATPase inhibitory activity was found in the large molecular weight compounds (>1 Kd) in plasma. The low inhibitory activity in the larger molecular weight fractions of plasma suggested that the low molecular weight inhibitor might be masked by association with a carrier protein or incorporation in a precursor molecule that requires further in vivo metabolism before its activity could be expressed. Pre-treatment of the >50 kD plasma fraction with mercaptoethanol followed by application of the plasma fraction to SDS-PAGE, yielded a 12,000 dalton protein band, identical in locus to the Na-K-ATPase inhibitor isolated from mercaptoethanol-treated plasma as described by Weiler et al., *Clin. Res.*, supra.

These reports attest to the difficulty of isolating natriuretic substances from plasma and urine. Because of the variety of procedures used to attempt to purify such substances, verification that a putative natriuretic substance having a particular molecular weight is the "native" compound having biological activity in vivo has not been possible. Correlation of low molecular weight natriuretic substances with disease states such as hypertension, is also hampered by the absence of a protocol that preserves the relationship of low molecular weight substances with "carrier" proteins or precursor proteins that exist in vivo. In addition, comparison of substances isolated from plasma by various researchers, and between substances isolated from plasma with those from urine is tenuous at best. Substances found in the urine may be altered, for example by the kidneys, such that the active form of a NH circulating in the plasma is different from the NH isolated from urine.

Correlation of putative NH substances with various diseases, including hypertension, has been attempted. In essential hypertension, there is preliminary data which point to a relationship between circulating levels of pump inhibitors and body volume status. Hamlyn et al., supra, reported an inverse correlation between the total level of plasma Na-K-ATPase inhibitors and renin activity, which is assumed to be suppressed in the presence of volume expansion. Devynck et al., ("Clinical and biochemical approach of a circulating Na-pump inhibitor", *J. Physiol.* 79:538–541 (1984)) reported that not only is there an increase in the level of circulating pump inhibitors in the plasma of untreated hypertensives as compared to normotensives, but this increased level is reduced toward normal by treatment with diuretics.

Additional studies suggest an association of the hypothalamic-renal NH with hypertension. For example, plasma from patients with low renin hypertension has been shown to contain more of the pump inhibitor, as measured directly by Na-K-ATPase inhibition (Hamlyn et al., "A circulating inhibitor of Na$^+$ associated with essential hypertension", *Nature* 300:650–652 (1982); Huot et al., "Sodium-potassium pump activity in reduced renal mass hypertension", *Hypertension* 5:94–100 (1983) and MacGregor et al., "Evidence for a raised concentration of a circulating transport inhibitor in essential hypertension", *Br. Med. J.* 283:1355–1365 (1981)), or indirectly by reduction of ouabain-sensitive sodium efflux from leukocytes (Edmondson and MacGregor, "Leucocyte cation transport in essential hypertension: its relationship to the renin-angiotensin system", *Br. Med. J.* 282:1267–1269 (1981)), than plasma from other hypertensives and normotensives. Moreover, in animals with various models of experimental hypertension, pump activity in blood vessels (as measured by ouabain-sensitive Rb$^+$ uptake) is reduced below that of normal controls (Haddy et al., "Humoral factors and the sodium-potassium pump in volume-expanded hypertension", *Life Sci.* 24:2105–2118 (1979)). Based on such observations, researchers have proposed that essential hypertension may be due to a hereditary defect in the kidney's ability to excrete sodium, thus leading to volume expansion and increased release of natriuretic hormone, which causes vasoconstriction via inhibition of the sodium pump in vascular smooth muscle cells, with an attendant increase in intracellular sodium and calcium. (Blaustein, "Sodium ions, calcium ions, blood pressure regulation and hypertension: a reassessment and a hypothesis", *Am. J. Phsiol.* 232:C165–C173 (1977); and "Role of a natriuretic factor in essential hypertension: An hypothesis", *Ann. Int. Med.* 98:785–792 (1983); De Wardener and MacGregor, "The relation of a circulating transport inhibitor (the natriuretic hormone?) to hypertension", *Medicine* 62:310–326 (1983)).

A few studies have also examined the effects of renal failure and dialysis on the circulating levels of natriuretic compounds or pump inhibitors. Bourgoignie et al. ("The presence of a natriuretic factor in urine of patients with chronic uremia. The absence of the factor in nephrotic uremic patients", *J. Clin. Invest.* 53:1559–1567 (1974)) reported that gel filtration fractions of serum or urine from patients with chronic renal failure produced a striking natriuresis in test animals. When serum fractions from the same patients in a nephrotic state were tested, no natriuresis was observed. This suggests that the volume status rather than uremia led to accumulation of a natriuretic substance. Boero et al. ("Erythrocyte Na, K pump activity and arterial hypertension in uremic dialyzed patients", *Kidney Int.* 34:691–695 (1988)) reported that RBC Na, K pump activity was lower in uremic patients than in normals, while serum from uremic patients inhibited ouabain-sensitive sodium efflux in normal RBC. Kelly et al., "Endogenous digitalis-like factors in hypertension and chronic renal insufficiency", *Kidney Int.* 30:723–729 (1986)) found that levels of digoxin-like immunoreactivity and Na-K-ATPase inhibitory activity in deproteinized plasma were increased in hypertensive patients with mild renal failure, whereas plasma levels in dialysis patients were not different from controls. An observed increase in Na-K-ATPase inhibitory activity was attributed to a rise in two out of three plasma fractions previously described. Devynck et al. ("Circulating inhibitor of sodium active transport in essential hypertension and volemic expansion", *Arch. Mal Coeur* 78:1691–1695 (1985)), on the other hand, found that plasma levels of a digitalis-like compound (measured by $^3$H-ouabain displacement) were elevated in renal failure patients requiring dialysis but these levels were reduced by the dialysis procedure, and the reduction in activity of this compound was proportional to the weight lost during dialysis. Krzesinski et al. ("Arguments for the presence of a Na-K-ATPase inhibitor in the plasma of uremic and essential hypertensive patients", *Clin. Exp. Physiol.* 79:538–541 (1984)) also reported the presence of a natriuretic factor in plasma of uremic subjects, the activity of which was reduced during dialysis in proportion to weight loss, attesting to the relationship between the circulating levels of this factor and body volume status.

Research conducted by Weiler et al., (*Clin. and Exper. Theory and Practice*, 1985, supra) compared the pattern of urinary Na-K-ATPase inhibitors in hypertensives and normal controls following sequential Sephadex column and C18 reverse phase separations. The results demonstrated that one, low molecular weight Na-K-ATPase inhibitor was present to an equal degree in hypertensives and normal subjects, whereas an earlier eluting low molecular weight inhibitor and all identifiable larger-sized components were increased in hypertensives. These data suggested that partial inhibition of enzymatic conversion of a precursor low molecular weight NH to the final form might be a factor in some forms of essential hypertension (defined as persistent hypertension without a currently definable etiology). Subsequent work identified a high molecular weight Na-K-ATPase inhibitor in mercaptoethanol-extracted plasma that altered in quantity with disease states (Weiler, *Clin. Res.*, supra). The intensity of a protein band of approximately 10,000 daltons was observed to increase in plasma from patients with primary aldosteronism and chronic renal failure, while decreasing in congestive heart failure. The band intensity returned toward normal after treatment of chronic heart failure. Upon further characterization by extraction and semi-purification on HPLC, one peak which contained the protein band was shown to be a potent inhibitor of Na-K-ATPase. These results demonstrated appropriate directional changes in the quantity of the high molecular weight form of circulating Na-K-ATPase inhibitor in disease states characterized by increased (primary aldosteronism and chronic renal failure) or decreased (congestive heart failure) central volume. In contrast, studies of alpha-h ANP have shown that this natriuretic material increases rather than decreases in CHF (Tikkanen et al., "Plasma atrial natriuretic peptide in cardiac disease and during infusion in healthy volunteers", *Lancet* 2:66 (1985)), implying that circulating Na-K-ATPase inhibitors may be of greater pathophysiological significance in this disease state.

In further studies, correlation of the high molecular weight inhibitor (approximately 12,000 K daltons) with hypertension has been found (Weiler et al., "Circulating high molecular weight form of Na-K-ATPase inhibitor:changes in disease", *Clin. Res.* 34:90A (1986); Gonick et al., "High and Low Molecular Weight Plasma Na-K-ATPase Inhibitors (NKAI) in Hypertension, presented at post-congress Satellite Symposium on Natriuretic Hormones in Hypertension, following the Xth International Congress of Nephrology, London, England, August (1987); and Weiler et al., "High Molecular Weight (HMW) Plasma Na-K-ATPase Inhibitor (NKAI) in Essential Hypertension (EH)", abstract, Proceedings of the Third Annual Meeting of The American Society of Hypertension in New York, June 1988 (*Amer. J. Hypertension* 1(3) Part 2:47A (1988)). In these studies, plasma from patients with essential hypertension, normotensive controls and normotensive controls with a family history of hypertension was first separated by Amicon® filtration into high and low molecular weight plasma fractions (less than 1,000 daltons). The low molecular weight inhibitors were further separated by C18 Sep-Pak cartridges using a 10% step-wise acetonitrile gradient, while the high molecular weight inhibitors were separated on Sephadex G-75 columns. All fractions were tested for Na-K-ATPase inhibitory activity after pretreatment with formic acid and mercaptoethanol. The concentration of the high molecular weight inhibitor was 30 fold the concentration of the low molecular weight inhibitor, confirming the predominance of the high molecular weight natriuretic material in hypertensive patients. The active fraction of the high molecular weight inhibitors was shown to contain a 12 kD protein band on SDS-PAGE, which was a potent inhibitor of Na-K-ATPase, displaced $^3$H-ouabain from its Na-K-ATPase receptor, but did not cross-react with ANF antibody. The high molecular weight inhibitor, but not the low molecular weight inhibitor, correlated positively with diastolic blood pressure and inversely with the natural log of renin. SDS PAGE separation of plasma from these subjects confirmed that patients with essential hypertension had higher staining intensities of the 12 kD compound than normal controls. Normotensive controls with a family history of hypertension had intermediate staining intensities of the 12 kD band. Significant differences were found between the mean concentrations of the high molecular weight inhibitor (12 kD compound) and low molecular weight inhibitors (less than 1 kD) between hypertensive and normal patients. Of the patients with essential hypertension approximately 60% had elevated plasma levels of the 12 kD compound relative to controls. These data clearly demonstrate the key role of the high molecular weight natriuretic hormone in the pathogenesis of hypertension.

With respect to other diseases such as congestive heart failure information is scarce regarding the role of the sodium transport inhibiting natriuretic hormone. Studies have demonstrated that a natriuretic substance found in an ultrafiltrate of normal urine was absent in the urine of patients with congestive heart failure (Kruck and Kramer, "Third factor and edema formation", *Contr. Nephrol.* 13:12–20 (1978)) and Kramer and Kruck, "Plasma natriuretic activity in oedematous states", *Proc. Eur. Dial. Transplant. Ass.* 12:321–329 (1976)). These studies also demonstrated that plasma and urine fractions from normals obtained following separation on Sephadex G-25 columns, consistently reduced short-circuit current when applied to the serosal surface of frog skin, whereas plasma and urine fractions obtained from patients with congestive heart failure lacked this effect. These results indicate that patients with congestive heart failure have a deficiency of a natriuretic, transport inhibiting substance which may be the hypothalamic-renal natriuretic hormone.

In view of the apparent association between the presence of natriuretic substances and disease and the long standing difficulty of identification and purification of such substances, it would be useful to provide reproducible methods for purifying Na-K-ATPase inhibiting substances having natriuretic activity that permit correlation with disease states and to provide the substances for diagnostic and therapeutic applications.

SUMMARY OF THE INVENTION

Accordingly, the present invention provides a substantially pure Na-K-ATPase inhibitor having vasoconstrictive activity and characterized by a molecular weight of approximately 408 daltons isolated from human plasma. This 408 dalton substance is associated with a 12,000 dalton compound having Na-K-ATPase inhibitory and natriuretic activity.

The invention further includes methods for isolating Na-K-ATPase inhibitory substances of molecular weight less than 500 daltons, including a 408 dalton Na-K-ATPase inhibitor having vasoconstrictive activity from the purified 12 kD compound. In a first embodiment the low molecular weight Na-K-ATPase inhibitory substances are obtained from plasma by a) filtering chilled plasma containing high and low molecular weight Na-K-ATPase inhibitory substances from a subject to eliminate substances of molecular weight less than 1,000 daltons to form a retentate containing substances of greater than 1,000 daltons molecular weight;

b) treating the retentate with formic acid and mercaptoethanol to release a 12 kD protein that inhibits Na-K-ATPase, displaces $^3$H ouabain and possesses natriuretic properties from larger molecular weight binding proteins; c) filtering the treated retentate to remove substances having a molecular weight greater than 30,000 daltons to form a filtrate; d) alkalinizing the filtrate to release low molecular weight Na-K-ATPase inhibiting substances from the 12 kD compound; e) separating the alkalinized filtrate using reverse-phase high performance chromatography to form semi-purified low molecular weight natriuretic Na-K-ATPase inhibitor substances. The semi-purified substances are then further purified by high resolution reversed phase HPLC with electrochemical detection followed by desalting and chromatographic separation using separate elution solvent systems of 100% water/0% acetonitrile/0.1% trifluoroacetic acid and 80% water/20% acetonitrile/0.1% trifluoroacetic acid to purify two low molecular weight substances having Na-K-ATPase inhibitory activity. One of these substances elutes in the 100% water/0% acetonitrile/0.1% trifluoroacetic acid solvent, has a molecular weight of 408 daltons as determined by FAB mass spectroscopy. Each low molecular weight compound inhibits Na-K-ATPase. A preparation containing both low molecular weight compounds displaces $^3$H ouabain and causes vasoconstriction in vitro.

In a second and preferred embodiment, the alkalinized filtrate is directly chromatographed on a cartridge solid phase using the water/acetonitrile/trifluoroacetic acid solvent system to obtain the 408 dalton Na-K-ATPase inhibitor and the second (later eluting) compound. These fractions are then subject to electrochemical detection to detect the 408 dalton compound and the second low molecular weight inhibitory compound.

The invention also provides a monoclonal antibody reactive with the purified 12 kD Na-K-ATPase inhibitor compound or 408 dalton compound and an in vitro assay method using the antibody for detecting elevated or decreased amounts of the 12 kD compound or the 408 dalton compound in a subject to permit determination of the relationship of the amount of the 12 kD or 408 dalton compound to disease associated with elevated or decreased amounts of these compounds.

A diagnostic kit including the antibody and a conjugate of a detectable label and a specific binding partner of the antibody is another embodiment of the invention.

A further embodiment of the invention is a method for treating disease caused by binding of Na-K-ATPase inhibitors in vivo by administering a pharmaceutically effective amount of an antagonist of the 12 kD compound or the 408 kD compound in a physiologically compatible pharmaceutical carrier to a subject to interfere with the biological activity of the 12 kD compound or the 408 kD compound, for example by binding to the in vivo receptors for these compounds.

Another embodiment of the invention provides a method for treating disease caused by a deficiency of the 12 kD compound or the 408 dalton compound by administering a pharmaceutically effective amount of the 12 kD compound or the 408 dalton compound in a physiologically compatible pharmaceutical carrier to a subject to eliminate the deficiency.

Still another embodiment of the invention is a method for detecting elevated or decreased amounts of low molecular weight Na-K-ATPase inhibiting substances including the 408 dalton compound in a subject by electrochemical detection of plasma samples from a subject using water/acetonitrile/trifluoroacetic acid solvents to identify the amount of these substances present in the subject.

DETAILED DESCRIPTION OF THE INVENTION

Figure 1:
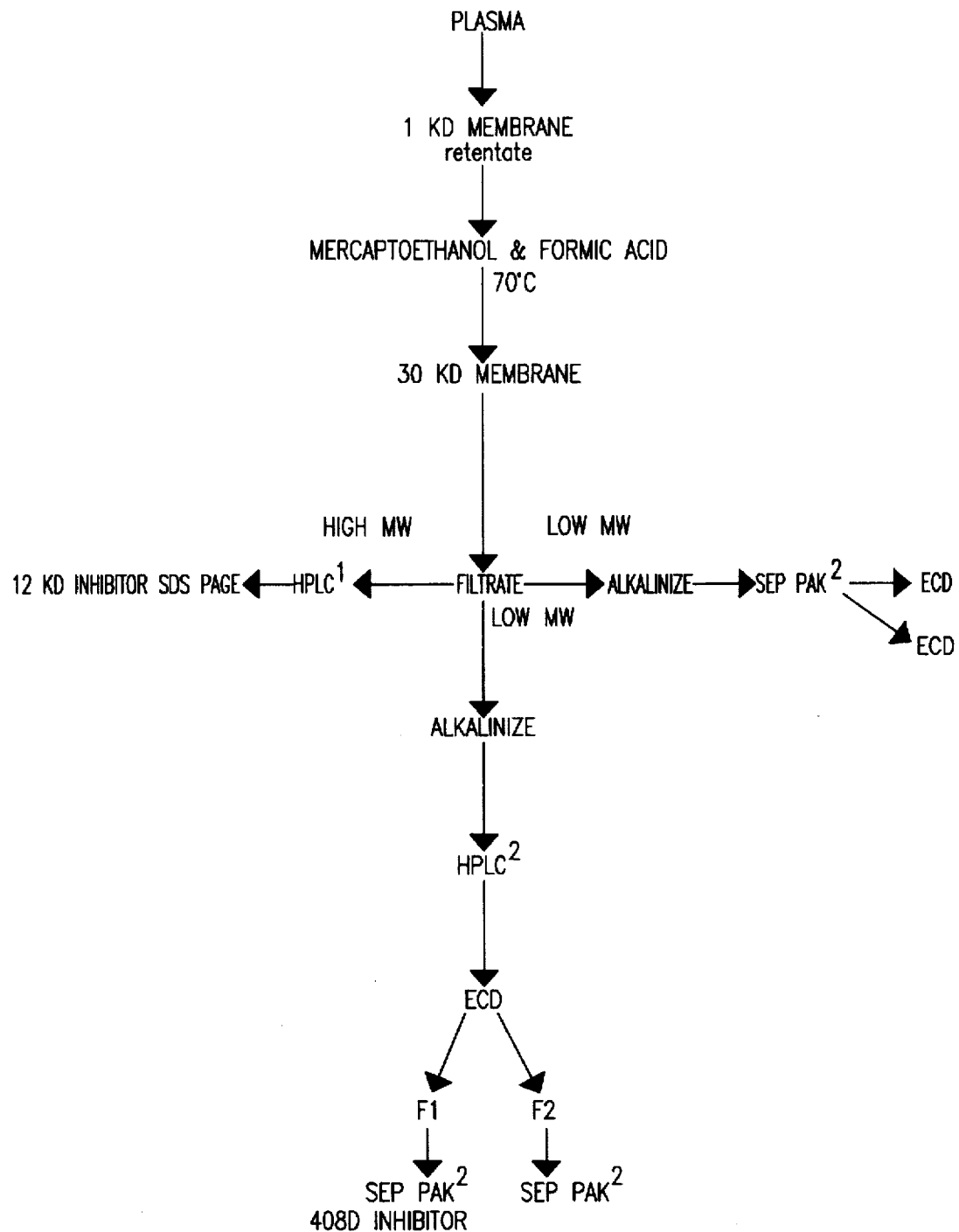
FIG. 1 is a flow chart illustration of the purification methods of the invention for obtaining semi-purified 12 kD Na-K-ATPase inhibitor and low molecular weight inhibitory substances as described infra.

In order that the invention herein described may be more fully understood, the following detailed description is set forth.

The invention is directed to the identification and purification of low molecular weight Na-K-ATPase inhibiting substances having natriuretic properties found in human plasma and urine.

In accordance with the present invention, a low molecular weight natriuretic substance associated with a higher molecular weight carrier protein is substantially purified from human plasma by a multi-step procedure that includes passage through filtration membranes and reverse-phase HPLC purifications. Detection of the low molecular weight natriuretic substances is enabled using electrochemical detection. The purified material inhibits Na-K-ATPase and has natriuretic activity. The low molecular weight natriuretic Na-K-ATPase inhibitor is associated with a "carrier" protein of approximately 12 kilodaltons (kD) molecular weight, which is in turn associated with higher molecular weight proteins (greater than 30 kD) in plasma. Previous attempts at purifying low molecular weight substances having natriuretic and Na-K-ATPase inhibitory activity have resulted in isolation of a variety of putative natriuretic substances from plasma and urine of different molecular weights, possibly because of the use of different procedures for purification of the material. The present invention provides a reproducible method for obtaining a purified low molecular weight Na-K-ATPase inhibiting substance with natriuretic properties from human plasma. The sequential procedures used to isolate the 12 kD carrier protein and to then separate the low molecular weight substance from the carrier protein and correlation of the presence of the carrier protein in plasma with various disease states, demonstrate that the low molecular weight material is an active form of natriuretic material associated with diseases such as hypertension. The additional findings disclosed herein which show decreased amounts of a low molecular weight Na-K-ATPase inhibitory substance in urine from congestive heart failure patients suggest that a deficiency of low molecular weight natriuretic substances, which may be the same or similar to that isolated from plasma, may contribute to the salt retention characteristic of this disorder.

Low molecular weight substances with Na-K-ATPase inhibitory activity are separated from the 12 kD carrier protein by a series of purification steps as described in detail in Example I, infra using reverse-phase HPLC and eluting with acetonitrile/water gradients. Electrochemical detection is used to visualize the low molecular weight Na-K-ATPase inhibitor substance. The material is then analyzed by Fast Atom bombardment (FAB) mass spectroscopy and Nuclear Magnetic Resonance (NMR) to determine the molecular weight and chemical structure of purified low molecular weight Na-K-ATPase inhibitory substances. Using these procedures, a substantially pure Na-K-ATPase inhibitor substance having a molecular weight of approximately 408 daltons was obtained.

A general description of the identification and purification of the 12 kD compound with its associated low molecular weight substances from plasma and the subsequent purification of the low molecular weight (408 dalton) Na-K-ATPase inhibiting substance is provided below.

Plasma Sample

It is desirable to start with a sample of plasma having as high a level of natriuretic Na-K-ATPase inhibitory substances as possible. We have observed that the staining intensity of the 12 kD band after SDS PAGE analysis of plasma from patients with primary aldosteronism is consistently stronger than in any patient with essential hypertension. Quantitation of Na-K-ATPase inhibitory activity from the 12 kD band obtained from one patient with primary aldosteronism revealed a level that was 8 times higher than the mean of the levels of high molecular weight compound found in patients with essential hypertension. This suggests that primary aldosteronism is the specific condition associated with the highest levels of the 12 kD compound as a result of sodium retention because of excess levels of aldersterone. Therefore, plasma from patients with primary aldersteronism is the preferred source for high molecular weight natriuretic substances for purification. Alternatively, patients suffering from essential hypertension in which elevated amounts of Na-K-ATPase inhibitor substances are present may be used. Plasma is obtained from a subject, for example, a human subject suffering from primary hyperaldosteronism, and is preferably kept chilled and collected in the presence of an anticoagulant such as EDTA and a proteinase inhibitor such as Trasylol®, to avoid enzymatic degradation and the loss of high molecular weight natriuretic substances or pump inhibitors from the preparation. The chilled plasma is then subject to ultrafiltration.

Ultrafiltration

In order to separate out high and low molecular weight Na-K-ATPase inhibitory activity and characterize the molecular size of the Na-K-ATPase inhibitory fractions of interest, chilled plasma samples are placed on different sized porous solid phases with molecular weight cut-offs ranging from 500 daltons to 50 kD. Suitable solid phases for use in the procedures of this invention are filter membranes such as Amicon® membranes available from Amicon, Lexington, Mass. To avoid early separation and loss of the low molecular weight inhibitor substances, it is preferable that the plasma is not treated prior to ultrafiltration. The ultrafiltration procedure is initially carried out using a filtering solid phase such as an Amicon® membrane with a 1 kD molecular weight cutoff, under 8 psi of $N_2$ pressure at 4° C. in a cold box. The resulting retentate is then subjected to further purification procedures.

In addition to the use of Amicon® membranes for ultrafiltration, it is expected that other devices may be substituted for the pre-purification steps described above. Thus, it is expected that other solid phases may be used provided they have pores of a size that permits separation of materials of greater than 1 kD and 30 kD molecular weight.

Formic Acid and Mercaptoethanol Pretreatment

The resulting retentate is treated with 1M formic acid and 4% mercaptoethanol and heated to 70° C. for approximately 10 minutes. This treatment releases a 12 kD protein with Na-K-ATPase inhibiting and natriuretic properties and associated low molecular weight inhibitory substances from larger molecular weight binding proteins. The retentate is then passed through a 30 kD membrane to remove substances having a molecular weight greater than 30 kD. The filtrate is then collected and lyophilized to dryness, and reconstituted in distilled water.

The resulting filtrate containing small amounts of low molecular weight Na-K-ATPase inhibitory and larger amounts of high (12 kD) molecular weight Na-K-ATPase inhibitory substances is then subjected to further purification procedures depending on whether one wishes to obtain the 12 kD Na-K-ATPase inhibitor compound with associated low molecular weight (less than 500 dalton) substances or purified low molecular weight inhibitory substances. These procedures are outlined in FIG. 1.

I. Purification of 12 kD Compound

The high molecular weight Na-K-ATPase inhibitory compound of approximately 12 kD molecular weight is obtained by separating the filtrate containing larger amounts of high molecular weight materials and smaller amounts of low molecular weight materials using reversed phase high performance liquid chromatography.

Reversed Phase High Performance Liquid Chromatography (HPLC)

Reversed phase HPLC is performed according to established procedures such as those described by Rivier et al., "Reversed-phase high-performance liquid chromatography of insulins from different species", *J. Chromatog.* 268:112–119 (1983); and Rivier et al., "Reversed-phase high-performance liquid chromatography: preparative purification of synthetic peptides", *J. Chromatog.* 288:303–328 (1984)) with modifications.

Alternatively, size exclusion columns, e.g. Ion Pak™ and OH Pak™ (Alltech Assoc., Inc., Deerfield, Ill.), anion exchange, e.g. Aquapore™ AX300 (Pierce Chemical Co., Rockford, Ill.), and cation exchange columns such as Aquapore™ CX300 (Pierce) may be used for pre-purification of the inhibitor substances. In addition, ion exchange chromatography, e.g. on Mono-Q or Mono-S columns (Pharmacia, Sweden) or chromatofocusing, e.g. on mono-P columns (Pharmacia) may be used.

The HPLC procedure is preferably conducted at room temperature. All solvents used are HPLC grade and are degassed. HPLC can be conducted under acidic, neutral or alkaline (pH 12) conditions.

The HPLC column is first equilibrated with triple distilled water. 100 µl of the inhibitory material obtained from the preceding procedures is applied onto a C18 silica gel column such as those available from (Alltech) using a Rheodyne (Alltech) injection valve. C4 to C18 columns may be used. Stationary phases consisting of silica gel are preferred. The mobile phase is preferably a gradient of an increasing concentration of a water-miscible organic solvent such as acetonitrile. Short chain alcohols, e.g. ethanol, propanol or isopropanol, in water, may also be used. Preferably, elution of the 12 kD inhibitory compound is achieved using a linear water/acetonitrile gradient of from 0% to 100% acetonitrile (water of from 100% to 0%) for 20 minutes at a flow rate of 2 ml/minute. One minute HPLC fractions are collected. Substances are detected in the column effluent by monitoring ultraviolet absorbance at 210 nm.

Each fraction obtained from the HPLC column is lyophilized and assayed for Na-K-ATPase inhibitory activity and $^3$H-ouabain displacement from purified Na-K-ATPase as described below. These tests established that a 12 kD compound having Na-K-ATPase inhibitory activity, and are able to displace $^3$H-ouabain, eluted at between approximately 48% and 50% acetonitrile in from about 8 to 10 minutes. The relative purity of the 12 kD inhibitory compound obtained is confirmed using SDS acrylamide gel electrophoresis (SDS-PAGE) performed according to the method described by Laemmli (*Nature* 277:680–685 (1970) ). Briefly, gradient gels (4% to 27%) are formed between two glass plates using a gradient mixer. Plasma samples (50 µl) are placed in a sample buffer (150 µl) containing SDS and β-mercaptoethanol and heated to 60° C. for 10 minutes. The mixture is then applied to the gradient gel and a constant current of 30 mA is applied until separation was complete (approximately 3½ hours). The slab gel is removed from the glass plates and stained with 0.01% Coomassie blue in a mixture of methanol, acetic acid and water. The gel is then destained in acetic acid, methanol and water and photographed.

II. Purification of low molecular weight inhibitor substances from 12 kD compound Alkalinization The filtrate obtained after ultrafiltration is alkalinized, for example using 0.8 M NaOH to a pH of approximately 12, to release low molecular weight (less than 500 daltons) Na-K-ATPase inhibitory substances associated with the larger 12 kD compound. The low molecular weight inhibitors are further purified by one of two methods (see FIG. 1).

A. In the first method, the alkalinized filtrate is separated on a C18 HPLC column using a linear water/acetonitrile gradient of from 0% to 100% acetonitrile as described above at a flow rate of 2 ml/minute (from 1 to 2 ml/minute), except that 0.1% trifluoroacetic acid (TFA) is added to each of the water and acetonitrile solvents. It is possible to omit the TFA and still obtain the desired elution pattern. Na-K-ATPase inhibitory material elutes off at approximately 2 minutes. This material is then subject to electrochemical detection (ECD) as described below.

Electrochemical Detection

HPLC with electrochemical detection (ECD) as described by Fallon et al., "Laboratory techniques in biochemistry and molecular biology", Volume 17, Chapters 3 and 11, pp. 23–42 and 260–270 (1987), provides a means of measuring oxidizable and reducible organic compounds and permits the detection of the low molecular weight Na-K-ATPase inhibitor substances of the invention. ECD has been shown to be particularly useful to detect biogenic amines such as catecholamines, 5-hydroxyindoles and O-methylated catechol metabolites.

Electrochemical detectors (LCEC) are operated by applying a fixed potential to the working electrode of a flow-through electrolysis cell and recording the current resulting from the oxidation or reduction of analytes as a function of elution time. LCEC detectors are referred to as "amperometric detectors". An amperometric detector produces a current which is proportional to the concentration of analyte as it is eluted from the HPLC column. This measurement requires that the applied potential results in the spontaneous and rapid oxidation or reduction of the analyte and that there be a provision for monitoring the electrolysis current. An amperometric measurement requires both an electrolysis cell and a control device called a potentiostat. A typical electrolysis cell contains three electrodes: a working electrode at which the analyte's electrolysis occurs; an auxiliary electrode at which the complimentary electrolytic reaction occurs; and a reference electrode that provides a stable potential to measure the potential of the working electrode.

All electrochemical detectors presently used with HPLC are amperometric detectors. The detectors hold the potential applied to the detecting test electrode constant and monitor the resultant currents as analytes flow past the detector. The applied potential is held constant and current is the variable measured for the procedure termed "amperometry". Typically, the test electrode causes oxidation or reduction to occur to some percentage of the analyte as it passes. Most amperometric sensors cause 1% to 5% of the passing analyte to undergo charge transfer (oxidation or reduction). When 100% of the analyte undergoes charge transfer, the electrode response is defined as coulometric.

The mobile phase acts as the supporting electrolyte in which the oxidation or reduction of one or more analytes occurs. The concentration of all buffers that can be employed for this technique ranges between 0.01 M and 1.0M in order to provide conductivity while maintaining a low background current. The measurement can be carried out between +1.0 and −1.0 volts (V) depending on the characteristics of the compound. In general, for the experiments set forth in the Examples, infra, a 0.1M buffer system was used, and measurements were carried out under conditions where the conditioning cell was at 0.2 V, electrode 1 was at −0.05 V and electrode 2 was at +0.40 V, with a gain of 10×1.

Catecholamines such as norepinephrine, epinephrine and dopamine are electrochemically detectible. To prevent interference with detection of the inhibitors, the catecholamines are adsorbed from plasma by passage through an alumina column. Norepinephrine and epinephrine elute later than the low molecular weight ATPase inhibitor which elutes first during ECD and will not interfere with detection. The low molecular weight inhibitor that elutes second during ECD elutes in essentially the same fraction as dopamine. Catecholamine, norepinephrine, epinephrine and dopamine are not present in the samples by the procedures described herein because they are removed earlier in the procedure by ultrafiltration.

ECD typically is conducted with the following equipment: Coulochem detector, dual electrode analytical cells, guard cell, high sensitivity analytical cell and conditioning cell and an HPLC system. ECD of the low molecular weight Na-K-ATPase inhibiting substances obtained by HPLC was performed with an ECD system from ESA, Inc. (Bedford, Mass.). The chromatography column used for the ECD separation was a 25 cm length (4.6 mm ID) reversed phase 3 micron high resolution C18 column from ESA held at 55° C. by a column heater. The materials are injected onto the column, for example using a Rheodyne (Alltech) injection system and are eluted off the column with an elution buffer provided by the manufacturer (ESA) consisting of methanol, 0.1M phosphate buffer and an ion pairing agent. Because the ECD system is non-destructive it permits the recovery of biologically active material.

The materials eluted from the column are then collected separately in pre-washed vials and the pH of each sample is preferably adjusted to a pH of 12 with, for example, 0.8M NaOH to bind the desired inhibitory material to the solid phase that is used to remove interfering ions from the ECD procedure, such as phosphate ions. A preferred system is a chromatographic system such as SEP PAK® cartridges (Waters Assoc., Milford, Mass.). The samples are applied to the solid phase and are eluted using water, acetonitrile and TFA. Prior to elution, the cartridge is washed with distilled water to remove phosphate ions or salts. The desired low molecular weight inhibitory compounds are then recovered in the eluate and tested for Na-K-ATPase inhibitory activity.

A preferred solvent system is a two step system using first 100% distilled water, 0% acetonitrile and 0.1% TFA followed by elution with 80% distilled water, 20% acetonitrile and 0.1% TFA. Using this elution system, the Na-K-ATPase inhibitory material with a retention time of 4.9 minutes from the ECD column eluted in the 100% distilled water, 0% acetonitrile solvent and the Na-K-ATPase inhibitory material with a retention time of 17.5 minutes was detected in the 80% distilled water and 20% acetonitrile and 0.1% TFA. The earlier eluting material (4.9 minutes during ECD) was determined to consist of the 408 dalton Na-K-ATPase inhibitory substance by FAB mass spectroscopy as described further, infra.

B. In the second and preferred method for obtaining purified low molecular weight Na-K-ATPase inhibitory substances, the alkalinized filtrate obtained after ultrafiltration of chilled plasma through a 1 kD membrane, pretreatment with formic acid and mercaptoethanol and filtration through a 30 kD membrane, is separated directly on a chromatographic solid phase such as the above-mentioned SEP PAK® cartridges and eluted from the cartridges after first washing with distilled water. The 100% distilled water/ 0% acetonitrile/0.1% TFA solvent system is used to obtain the earlier eluting (4.9 minutes) low molecular weight Na-K-ATPase inhibitory compound (408 daltons) and the 80% distilled water/20% acetonitrile/0.1% TFA solvent is used to obtain the later eluting (17.5 minutes) low molecular weight Na-K-ATPase inhibitory compound. Each fraction is lyophilized and assayed for Na-K-ATPase inhibitory activity as described below.

The material obtained from each elution is then separately subjected to ECD on a 3µ HPLC column as described above to confirm the purity of each compound.

FAB Mass Spectroscopy Structure Analysis

FAB mass spectra (FAB MS) analysis to determine the molecular weight of the substances eluting from the HPLC columns is performed according to the procedures described by Tamura et al., "Isolation and Characterization of a Specific Endogenous $Na^+$, $K^+$-ATPase Inhibitor from Bovine Adrenal", Biochem. 27:4244–4253 (1988)) with modifications as described in Example I, infra. FAB mass spectroscopy analysis of the purified substance eluting in the 100% water/0% acetonitrile/0.1% TFA solvent demonstrated a molecular weight of 408 daltons for this substance.

The biological activities of the compounds obtained by the above purification procedures are assayed by the following methods:

Determination of Na-K-ATPase Inhibition

ATPase inhibitory activity is determined using a purified Na-K-ATPase enzyme derived from hog cerebral cortex, purchased from Sigma Chemical Co. (St. Louis, Mo.). Since maximum activity of this enzyme preparation is obtained in the presence of approximately 1 mM ATP and 20 mM $K^+$, incubation tubes contain 0.125 ml of substrate solution to provide final concentrations of 1 mM ATP, 1 mM $Mg^{+2}$, 10 mM imidazole-HCl buffer, pH 7.2, 100 mM $Na^+$, and 20 mM $K^+$, 1 mM ethylene glycol bis (β-aminoethylether)-N, N"-tetraacetic acid (EGTA). Dilutions of sample in the amount of 0.1 ml are added and each tube is incubated at 37° C. for 5 minutes. To start the reaction, 0.025 ml of enzyme preparation (25 mg of enzyme/ml) is added. The incubation is stopped after 15 minutes by adding ice-cold 10% trichloroacetic acid (TCA). After centrifugation (1700 g×5 minutes) 5 ml of supernatant was assayed for inorganic phosphate by the method of Fiske and Subbarow ("Colorimetric determination of phosphorous"J. Biol. Chem. 66:375–381 (1925)). In all instances, percentage inhibition was expressed as moles ouabain-equivalents per liter of plasma or urine or 24 hour urine sample.

Assay for Digoxin-Like Immunoreactivity

Although, as explained above, the information regarding digoxin-like immunoreactivity of putative natriuretic substances is sometimes contradictory, the presence or absence of such cross-reaction may be used to compare and distinguish natriuretic substances from each other. For Na-K-ATPase substances isolated from urine and plasma, the apparent digoxin concentrations, i.e. endogenous digoxin-like immunoreactivity, is determined radioimmunologically as follows.

The Digoxin Radioimmunoassay kit (Baxter Healthcare, Cambridge, Mass.) uses a Gamma Coat™ $^{125}$I procedure which is based on competition binding principles. Ten ml of Tris buffered saline containing bovine serum albumin, 0.02 M sodium azide, 4 µCi $^{125}$I-digoxin was added to 100 ml phosphate buffered saline with 0.02 M sodium azide as preservative. Fifty µl of digoxin standards, ranging from 0 ng/ml to 4 ng/ml and differing natriuretic hormone concentrations are incubated with 1 ml of tracer buffer. The mixtures are vortexed and then incubated in a water bath for 1 hour at 37° C. After 1 hour the aqueous phase is removed by aspiration or decantation. All tubes are counted in a gamma counter (Abbott Laboratories, Auto-logic, N, Chicago, Ill.) for 5 minutes with the window adjusted to $^{125}$ iodine.

$^3$H-Ouabain Displacement

Displacement of $^3$H-ouabain has been used to identify Na-K-ATPase inhibiting substances (Kelly et al., supra). The effect of natriuretic Na-K-ATPase inhibiting substances on $^3$H-ouabain binding to the Na-K-ATPase receptor enzyme are performed as follows: 200 µl Na-K-ATPase enzyme from hog cerebral cortex (Sigma Chemical Co., St. Louis, Mo.) approximately 1 mg protein) is incubated with $1 \times 10^{-8}$ Molar $^3$H-ouabain (approximately 120,000 counts; specific activity of 28 Ci/mmol (New England Nuclear, Boston, Mass.), in a buffer solution with a final concentration of 2 mM ATP, 2 mM $MgCl_2$, 100 mM NaCl, 1 mM EGTA, and 50 mM Tris-HCl (pH 7.4). After an incubation period of 60 minutes at 37° C., at which binding equilibrium was achieved, unlabeled ouabain at concentrations ranging from $5 \times 10^{-8}$ to $3 \times 10^{-6}$M or Na-K-ATPase inhibiting substances in amounts equal to 0.1 to 4 ml of original plasma volume is added. The final volume of the incubate is 1.0 ml. The reaction is stopped by addition of 1.0 ml ice-cold Tris-HCl buffer. Unbound $^3$H-ouabain is separated from protein-bound $^3$H-ouabain by a conventional filtration technique using Millipore filter GSTF with a pore size of 0.22 µm mounted on a Manifold Sampling Millipore apparatus No. 1225 connected to a water-suction pump. Complete removal of free $^3$H-ouabain is achieved by five washings with 2 ml buffer each time. $^3$H-ouabain bound to protein and retained on the filter is counted, for example, in an automatic Beckman LS-100 (Fullerton, Calif.) liquid scintillation counter at a counting efficiency of 44%.

Vascular reactivity assay

The effect of putative Na-K-ATPase inhibiting substances on vascular reactivity is tested in vitro. Studies have demonstrated that a low molecular weight urinary Na-K-ATPase inhibitor, had intrinsic vasoconstrictor properties, enhanced vasoconstriction produced by norepinephrine and angiotensin II, and its vasoconstrictor effect could be partially prevented by removal of calcium from the bathing solution (Weber et al., "Effects of human-derived sodium transport inhibitor on in vitro vascular reactivity", *J. Hypertension* 2(10):654–761 (1989)).

An in vitro vasoconstriction assay is also used to determine the vasoconstrictive effects of the substances isolated from plasma. The assay employs rabbit femoral arteries bathed in Krebs-bicarbonate solution. Viability of the preparation is confirmed by testing contractility after exposure to 60 mmol potassium. Constriction in response to ouabain-equivalents (determined in the Na-K-ATPase assay) of putative inhibitor substance is expressed in relationship to the enhancement of norepinephrine or angiotensin II effects or in the absence of these substances. Removal of calcium effects, for example by use of a calcium channel blocker such as nifedipine, is used to determine whether the vasoconstriction induced by the Na-K-ATPase inhibitory substance of the invention is calcium dependent.

Bioassay to Demonstrate Natriuretic Properties

Natriuretic properties of isolated putative natriuretic substances are assessed using an in vivo animal model, such as rats (Klingmuller et al., "Digoxin-like natriuretic activity in the urine of salt-loaded healthy subjects", *Klin. Wochenschr.* 60:1249–1253 (1982)). Urine samples are collected and analyzed for urinary sodium, potassium, chloride and urine volume after administration of test samples of the putative natriuretic substance. Urinary concentrations of sodium are determined using flamephotometry.

Using the above purification and assay procedures, as described in the Examples, infra, semi-purified 12 kD compound was isolated and shown to possess Na-K-ATPase inhibitory and natriuretic activity. This compound was previously demonstrated to correlate with various disease states including essential hypertension and primary hyperaldosteronism. From this 12 kD compound a low molecular weight (408 dalton) substance was purified and detected using ECD. This substance was shown to possess Na-K-ATPase inhibitory activity, to displace ouabain, stimulate vascular reactivity and to be distinct from digoxin-immunoreacting substances previously described.

Figure 5:
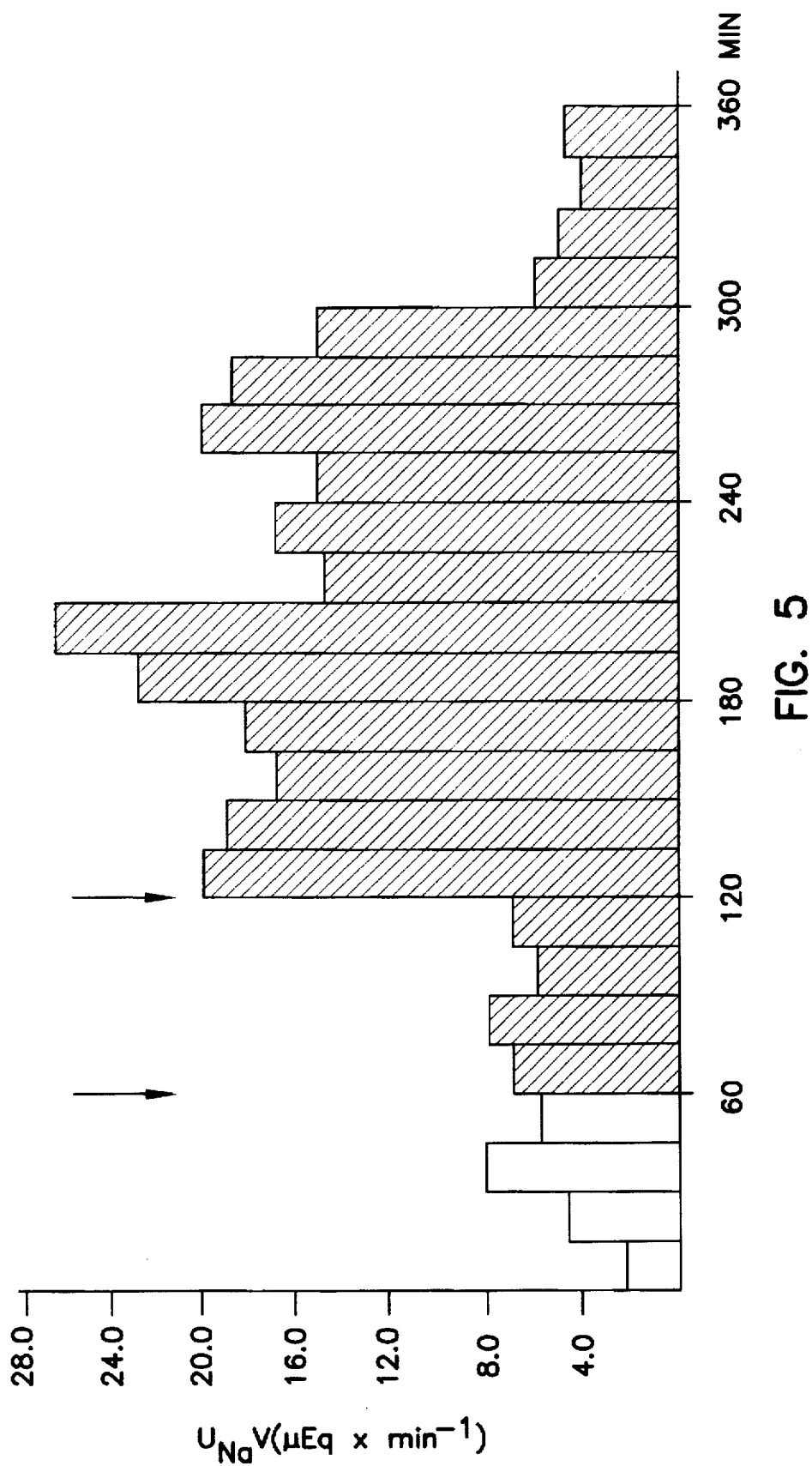
FIG. 5 is a bar graph showing the results of the natriuretic bioassay of semi-purified 12 kD Na-K-ATPase inhibitor preparation as described in Example I, infra.

Results of bioassay of semi-purified 12 kD material containing both high and low molecular weight Na-K-ATPase inhibiting substances from plasma indicated that both immediate and long lasting natriuresis was produced (see FIG. 5, infra). These data provide indirect evidence for the natriuretic activity of the 408 dalton Na-K-ATPase inhibitory substance of the invention. In addition, the 408 dalton plasma inhibitor was shown by HPLC separation to elute in the same fraction as a low molecular weight substance isolated from urine and deficient in patients during congestive heart failure and elevated in patients with essential hypertension. These results suggest that the urinary inhibitory is the same or structurally similar to the purified 408 dalton plasma inhibitor of the invention.

Determination of Structure

The determination of the molecular formula of the low molecular weight inhibitors of the invention is accomplished using Fast Atom Bombardment Mass Spectrometry followed by NMR as described by Tamura et al., "Isolation and Characterization of a Specific Endogenous $Na^+$, $K^+$-ATPase Inhibitor from Bovine Adrenal", *Biochemistry* 27:4244–4253 (1988)). Determination of the chemical structure of the 408 dalton Na-K-ATPase inhibitor of the invention permits the preparation by chemical synthesis of the compound and of antagonists and analogues for use in diagnosis and therapy.

Obtaining substantially pure fractions of low molecular weight natriuretic Na-K-ATPase inhibitor substance represents a significant improvement over previously described attempts to isolate natriuretic substances from plasma and urine. As a substantially pure substance, the low molecular weight natriuretic substance has utility which partially purified natriuretic substances do not. For example, the purified substance may be administered to treat disease states where a deficiency of the substance is manifest. The purified low molecular weight or 12kD inhibitor substances may be used as immunogen to prepare hybridomas producing monoclonal antibodies specifically reactive with the substance for diagnostic applications.

To enable large-scale production of the natriuretic substances using recombinant DNA techniques the first step is to clone the cDNA encoding the 12 kD inhibitor. Two approaches are feasible for generating the required probes. If enough natriuretic substance can be purified biochemically, microsequencing of the protein can be used to deduce the amino acid sequence of small regions. Degenerate oligonucleotides can then be generated from these regions and used either to screen a cDNA library prepared from the appropriate tissues or in the polymerase chain reaction (Mullis and Faloona, *Methods Enzymol.* 155:335–350 (1987)) to identify a small cDNA fragment within the natriuretic substance defined by the oligonucleotides.

Alternatively, a monoclonal antibody produced according to established procedures (e.g. Kohler and Milstein, "Continuous Cultures of Fused Cells Secreting Antibody of Pre-Defined Specificity", *Nature* 256:495–497 (1975)) raised against the epitope associated with activity of the 12 kD Na-K-ATPase inhibitory compound and associated low molecular weight inhibitory substances can be used to screen a cDNA library prepared, for example in bacteriophage lambda gt11 (Young and Davis, *Science* 222:728 (1983)). Immunopositive cDNA clones are sequenced by the dideoxy method of Sanger et al., (*Proc. Natl. Acad. Sci. USA* 74:5463 (1977)) as further described by Messing et al., *Nucleic Acids Res.* 9:309 (1981)) or by the method of Maxam et al., *Methods in Enzymol.* 65:499 (1980)).

To establish the identity of cDNA clones isolated by either of the above methods, the DNA sequence of the putative natriuretic inhibitor is compared to other gene sequences in GENBANK (assuming that other Na-K-ATPase inhibitors or similarly functioning substances have been identified, cloned and published). Alternatively, cDNA libraries are screened to obtain full-length cDNAs and tested individually in biological assays for Na-K-ATPase inhibition and/or natriuresis in test animals.

The techniques used to transform cells, construct vectors, extract messenger RNA, prepare cDNA libraries, and the like are well-established in the art, and most practitioners are familiar with the standard resource materials for specific conditions and procedures.

Applications of both the 12 kD and the low molecular weight natriuretic Na-K-ATPase inhibitor of the invention in experimental biology and clinical medicine, and in research in these areas, are abundant. The availability of purified Na-K-ATPase inhibitors and antibodies reactive with these inhibitors provides the ability to detect and treat various disease states associated with the presence of these substances.

Purified low molecular weight Na-K-ATPase inhibitory substances and/or purified 12 kD Na-K-ATPase inhibitory compound with associated low molecular weight compounds may be used as immunogen to generate hybridomas producing specific antibodies suitable for diagnostic applications. For example, monoclonal antibodies reactive with the compounds can be used to detect the substances as antigen in in vitro assays.

In vitro diagnostic methods include serologic detection of inhibitor, e.g. in blood samples. Such methods include well-known techniques in the art such as radioimmunoassays (RIA) or enzyme-linked immunosorbent assays (ELISA) wherein an antibody reactive with the inhibitor is used to detect the presence of the inhibitor in a fluid sample (Uotila et al., "Two-Site Sandwich Elisa With Monoclonal Antibodies to Human AFP", *J. Immunol. Methods* 42:11 (1981)).

Assays using the antibodies reactive with inhibitor substances can be used to detect the presence of and/or elevated amounts of the high and low molecular weight inhibitory substances in blood samples. This information may be used to define the cause of hypertension in patients with established hypertension and to screen for individuals predisposed to develop hypertension as a result of familial (genetic) inheritance patterns. Alternatively, the assay may be used to detect a deficiency of inhibitor substances which may indicate a predisposition to congestive heart failure. These assays include, but are not limited to, standard RIA techniques, both liquid and solid phase, as well as ELISA assays, immunofluorescence techniques, and other immunocytochemical assays (Sikora et al., (eds), *Monoclonal Antibodies*, pp. 32–52, Blackwell Scientific Publications, (1984)).

The invention also encompasses diagnostic kits for carrying out assays to detect the presence of elevated levels of, or a deficiency of natriuretic Na-K-ATPase inhibiting substances. Such kits include an antibody reactive with the substances, and a conjugate having a specific binding partner for the antibody and a label that produces a detectable signal. The reagents include ancillary agents such as buffering agents and protein stabilizing agents such as polysaccharides. The diagnostic kit can further include, where necessary, other components of a signal-producing system including agents for reducing background interference, control reagents and/or an apparatus or container for conducting the test.

An additional diagnostic method to detect the presence elevated amounts of the low molecular weight Na-K-ATPase inhibitory compounds or with a deficiency of these substances consists of the use of HPLC in combination with electrochemical detection to detect and measure the amount of inhibitory substances in plasma samples taken from a subject. Peak height and peak area for the low molecular weight substances eluted in the ECD procedure as described above are used for quantitation purposes in relationship to standards consisting of known amounts of the 408 dalton inhibitor and the second low molecular weight inhibitor separated from the 12 kD compound. Prior to the ECD measurement, catecholamines (which are also detected by ECD) are removed by adsorption to an alumina column. Total circulating low molecular weight Na-K-ATPase inhibitors are measured after deproteinization of plasma by boiling and acidification, for example to a pH of 3.5, to release the low molecular weight inhibitors from the 12 kD compound. Free (i.e. not bound to the 12 kD compound) circulating low molecular weight inhibitors are measured in untreated plasma. The amount of bound low molecular weight inhibitors is calculated as the difference between the measured total and free inhibitors. These measurements permit a comparison between the free and bound low molecular weight inhibitors which in turn can indicate whether a disease condition in a subject is related to the presence of elevated amounts or deficient amounts of the low molecular weight inhibitors.

The purified Na-K-ATPase inhibitors having natriuretic properties are also useful for therapeutic applications. The inhibitory substances can be used for treatment of disease conditions associated with the presence of elevated levels of the substances, for example, hypertension. To treat such diseases, antagonists of the inhibitory substance are prepared by chemical synthesis such that the antagonist will bind to the same receptor as the active substance but is slightly modified structurally so as to be biologically inactive once bound. The antagonist is administered to compete with the binding of the inhibitory substance in vivo to its receptor, thus interfering with its deleterious effects. Alternatively, non-competitive antagonists may be derived that bind near the receptor for the natriuretic substances and interfere with the ability of the receptor to bind the natriuretic substances. In addition, either the synthesized low molecular weight inhibitors or synthetic analogues of the inhibitors may be used to supply necessary levels of the substance in disease such as congestive heart failure where a deficiency of the substance is indicated.

An additional therapeutic application of the Na-K-ATPase inhibiting natriuretic compounds of the invention is a method of administering a compound which interferes with the synthesis and/or secretion of the 12 kD compound from its source in vivo, for example using a drug which targets the hypothalamus. In addition, a possible approach to therapy for diseases such as hypertension which may be associated with defects in the metabolism of the low molecular weight inhibitory compounds, is to accelerate metabolic conversion of the low molecular weight inhibitors to smaller substances which results in reduction of plasma levels of these compounds or in the production of substances that retain natriuretic activity but have lowered or no vasoconstrictive activity. This is accomplished, for example, by enhancing enzymatic processes that result in such metabolism of the compounds. This would result in the ability to treat hypertension by decreasing the circulating amounts of active Na-K-ATPase inhibiting and vasoactive compounds.

The present invention thus encompasses compositions, combinations and methods for treating human diseases such as hypertension associated with elevated amounts of Na-K-ATPase inhibiting substances possessing natriuretic properties, or for treating a disease such as congestive heart failure or cirrhosis with ascites, associated with a deficiency of such substances. For example, the invention includes pharmaceutical compositions for use in treating such diseases comprising a pharmaceutically effective amount of an antagonist or analogue of the inhibitor substance and a pharmaceutically acceptable carrier or adjuvant. Conventional carriers and adjuvants known in the art include human serum albumin, ion exchangers, alumina, lecithin, buffer substances such as phosphates, glycine, sorbic acid, potassium sorbate, and salts or electrolytes such as protamine sulfate. The compositions may additionally contain other therapeutic agents for treating the disease.

These compositions, including unmodified inhibitor substances, antagonists or analogues, are administered using conventional modes of administration including, but not limited to, intravenous, intraperitoneal, oral, intralymphatic, intramuscular, intravascular or topical administration. For some conditions it may be necessary to modify the compounds to facilitate gastrointestinal absorption.

The compositions of the invention for treatment of disease are administered in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application. The most effective mode of administration and dosage regimen for the compositions of this invention depends on the severity and course of the disease, the patient's health and response to treatment and the judgment of the treating physician. Accordingly, the dosages of the compositions should be titrated to the individual patient.

Initially, physiological ("normal") levels of the low molecular eight and 12 kD Na-K-ATPase inhibitory compounds are determined and samples from a subject are tested to determine presence of the inhibitor relative to normal physiological levels. Where the inhibitor is determined to be present in elevated amounts, antagonists are administered in a dosage sufficient to reduce blood pressure to normal. Alternatively, where samples from a subject indicate a deficiency of the inhibiting natriuretic substance relative to normal levels, analogues are administered to supplement the deficiency until normal levels or, if necessary, levels above normal, are reached and maintained, and the subject undergoes the desired natriuresis.

In order that the invention described herein may be more fully understood, the following examples are presented to illustrate the present invention and to assist one of ordinary skill in making and using the same. The examples are not intended in any way to otherwise limit the scope of the disclosure or the protection granted by Letters Patent hereon.

EXAMPLE I

Purification of Low Molecular Weight Natriuretic Na-K-ATPase Inhibiting Substances from Plasma This example describes the isolation and characterization of a high molecular weight (approximately 12 kD) compound that inhibits Na-K-ATPase and possesses vasoconstrictive and natriuretic properties, and the subsequent purification of low molecular weight substances, including a substance of approximately 408 daltons molecular weight that also inhibits Na-K-ATPase and induces vasoconstriction, from the semi-purified 12 kD compound.

Purification and Characterization of the 12 kD Na-K-ATPase Inhibitor

The 12 kD compound was purified from the plasma of hypertensive subjects and subjects with primary aldosteronism. Briefly, 250 ml of plasma was obtained from 2 essential hypertensive subjects and 2 patients with primary aldosteronism. Plasma samples were obtained in the morning. Blood was drawn in chilled tubes containing Trasylol-bacitracin (a proteinase inhibitor)-EDTA (an anticoagulant), immediately centrifuged in the cold, plasma separated and stored at −80° C. until tested.

In order to accumulate sufficient material to perform dose response assays of the 12 kD protein, pooled chilled plasma was first passed through a 1 kD Amicon® membrane to remove substances of molecular weight less than 1 kD. The retentate was treated with 1M formic acid and 4% mercaptoethanol and heated to 70° C. for 10 minutes to release the 12 kD compound with Na-K-ATPase inhibiting properties from larger molecular weight binding proteins. The retentate was passed through a 30 kD membrane to remove substances having a molecular weight greater than 30,000 daltons, and the filtrate was collected and lyophilized to dryness, then reconstituted in distilled water. The resulting material was then separated on a C18 reverse phase HPLC column (Spectra Physics, San Jose, Calif.) employing a linear water-acetonitrile gradient from 0% to 100% acetonitrile for a period of 20 minutes at a flow rate of 2 ml/minute. One minute HPLC fractions were collected and fractions were detected in the column effluent by monitoring ultraviolet absorbance at 210 nm.

A 12 kD protein band (determined to possess Na-K-ATPase inhibitory activity) was found at 48%–50% acetonitrile. The relative purity of this carrier compound was confirmed using SDS-PAGE, which yielded the 12 kD band and two minor bands of approximately 8 kD and 10 kD molecular weight. This material did not cross-react with ANF antibody.

Activity of 12 kD Carrier Protein

Figure 2:
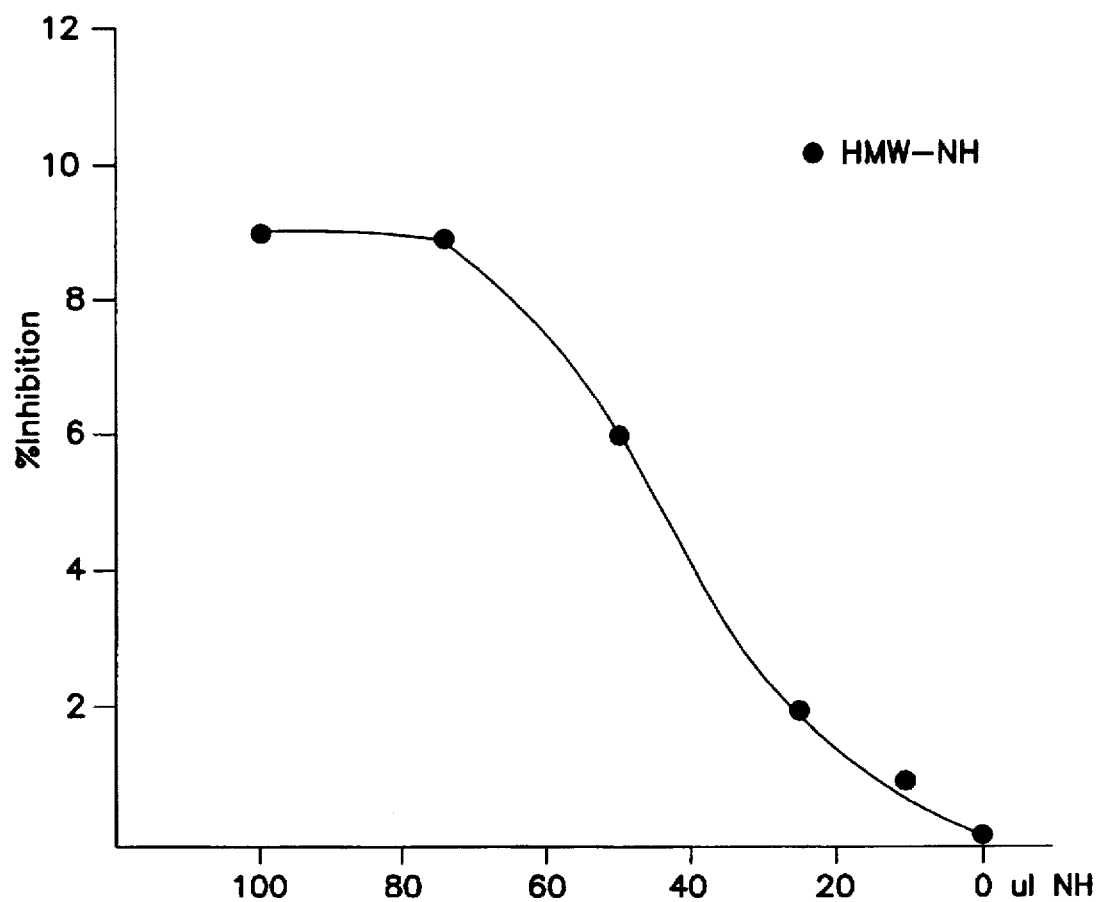
FIG. 2 is a graph of the Na-K-ATPase inhibition dose response curve for HPLC semi-purified 12 kD inhibitor, as described in Example I, infra.
Figure 3:
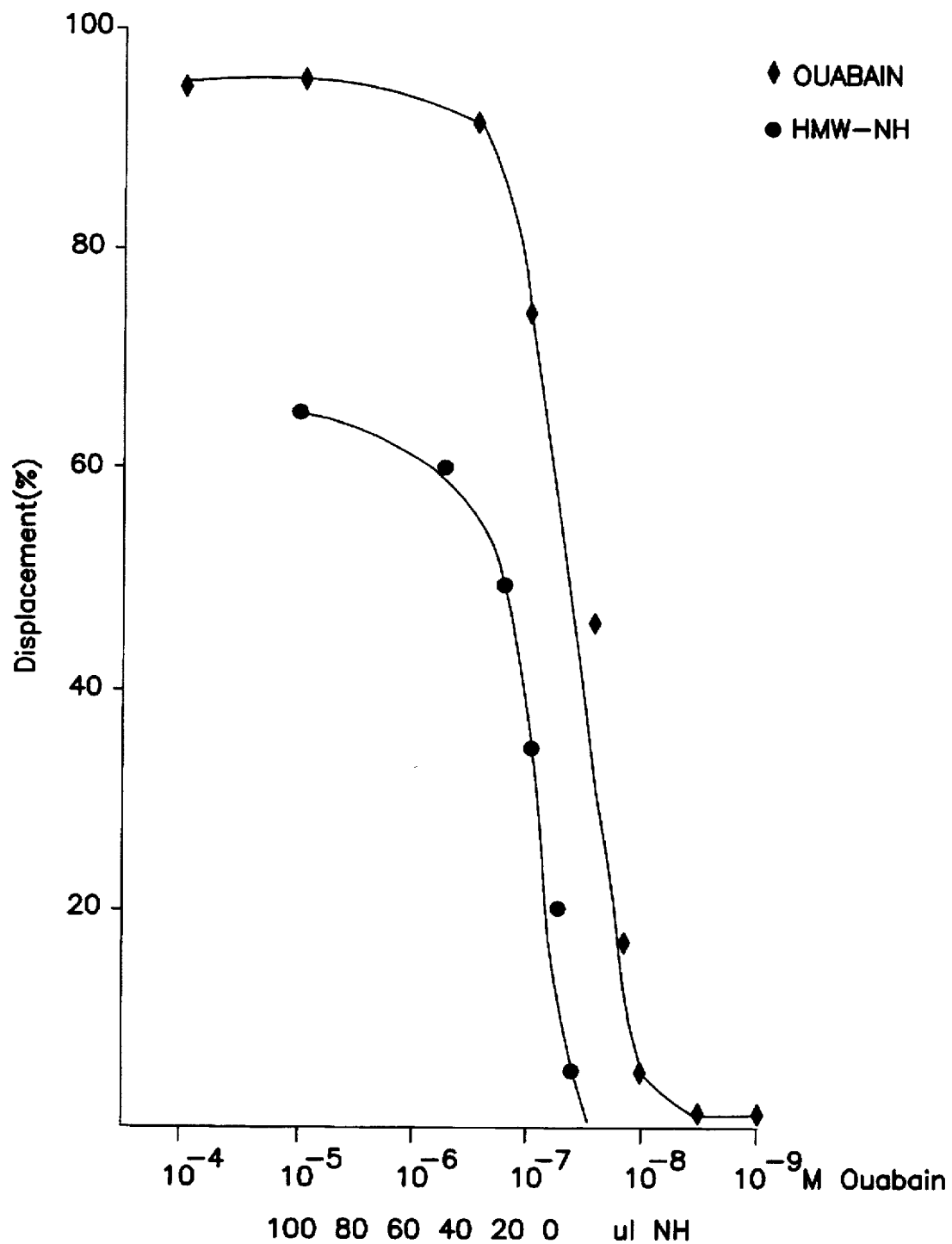
FIG. 3 is a graph of the $^3$H-ouabain displacement dose response curve for HPLC purified 12 kD inhibitor, as described in Example I, infra.
Figure 4:
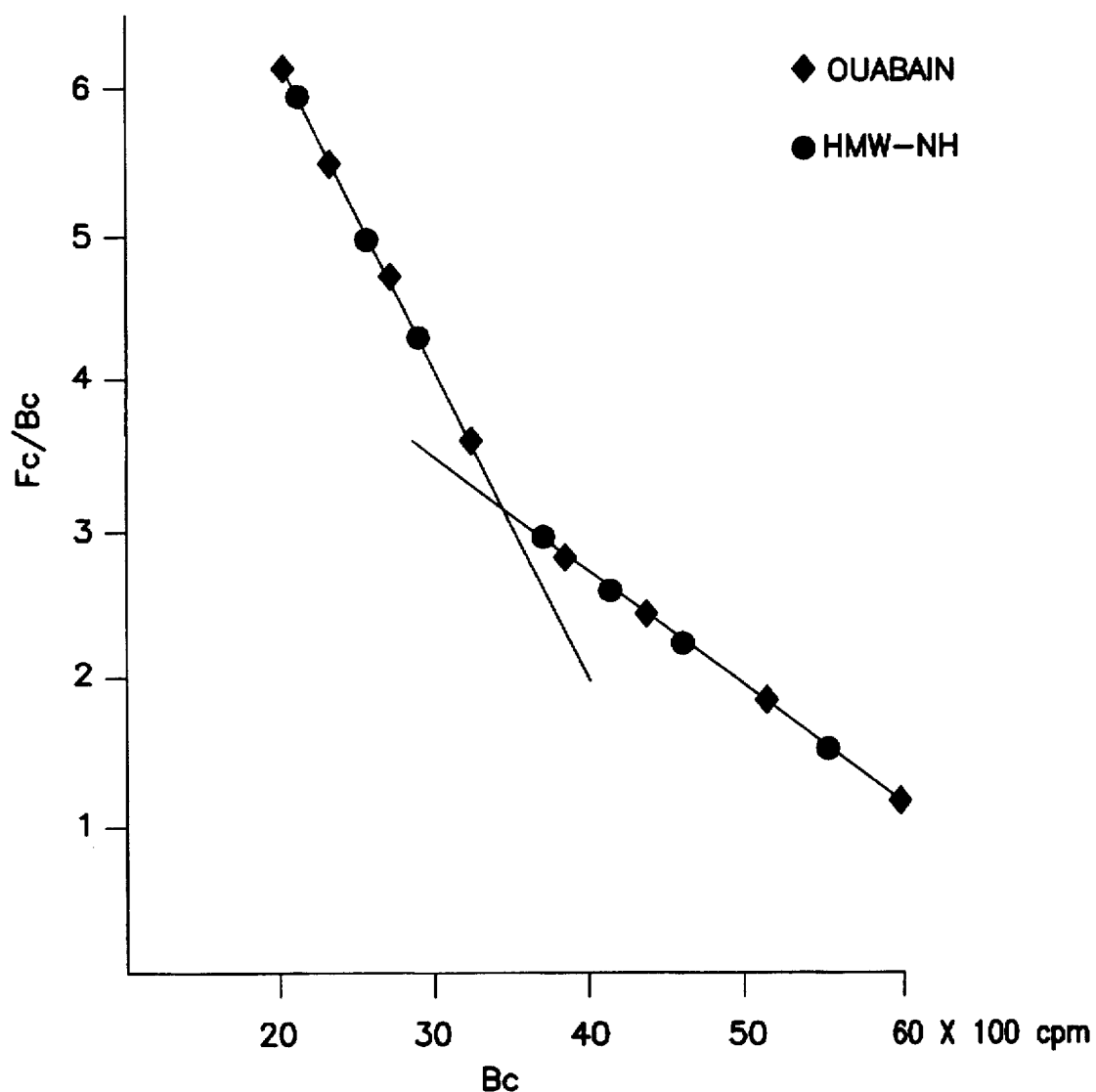
FIG. 4 is a Scatchard plot analysis of HPLC purified 12 kD inhibitor compared to ouabain, as described in Example I, infra.

The resulting preparation was then tested in assays for activity as represented by Na-K-ATPase inhibition and $^3$H-ouabain displacement from purified hog cerebral cortex Na-K-ATPase (Sigma Chemical Co., St. Louis, Mo.) as described above. Na-K-ATPase inhibitory activity and ouabain displacement were demonstrated as shown by the dose response curve for Na-K-ATPase inhibition shown in FIG. 2 and the $^3$H-ouabain displacement curve in FIG. 3. Scatchard plot analysis revealed that the 12 kD inhibitor bound to both high and low affinity receptors of purified Na-K-ATPase (FIG. 4).

Bioassay for Natriuretic Activity of 12 kD Na-K-ATPase Inhibitor Compound

Plasma was pooled from 2 hypertensive subjects, treated with formic acid and mercaptoethanol as described above, then applied to a Sephadex G-75 column and eluted with 10 mM ammonium acetate. A single fraction was shown to contain the Na-K-ATPase inhibitory material and the 12 kD protein band. This fraction was lyophilized for bioassay.

Natriuretic activity of the semi-purified material isolated from the pooled hypertensive plasma was assessed in a natriuresis bioassay using female Sprague Dawley rats weight 200–250 grams. Rats were previously fed a normal rat chow diet and had free access to food and water. On the day of the study animals were anesthetized with methohexital (50 mg/kg body weight intraperitoneally) or any other appropriate drugs listed in the guidelines. Polyethylene catheters (PE 50) were inserted into the jugular vein and transabdominally into the urinary bladder (PE 90). The animals were placed in individual restraining cages mounted on a triple beam balance. The animals were infused i.v. with 0.9% NaCl in 2.5% glucose solution at an infusion rate of 32–62 µl/min. Infusion rate was changed throughout the experiment in order to guarantee a constant body weight. Animals were allowed to recover from surgery for at least 2 hours prior to any urine collections. After the recovery period, 15 minute urine collection periods were started, and only when renal sodium excretion and urine minute volume were found to be stable, the actual experiment was initiated. A control solution (Tris-HCl, pH 7.4) with a volume ranging between 0.1 ml to 0.5 ml was injected into the test animal via the jugular vein over a period of 2 minutes and subsequently the collection of 15 minutes urine collection periods were started. Only when urinary sodium and urine minute volume was found to be stable during the control period a test sample, reconstituted in Tris-HCl buffer, pH 7.4 was injected slowly into the animal via the jugular vein. Following the injection of test sample at least eight 15 minute urine collection periods were collected. Each 15 minute urine collection period was then analyzed for urinary sodium, potassium, chloride and urine volume. Urinary concentrations of sodium and potassium were determined by flame-photometry. Results are shown in FIG. 5.

Clarkson et al. ("Two natriuretic substances in extracts of urine from normal man when salt-depleted and salt-loaded", *Kidney International*, Volume 10, pp. 381–394 (1976)) have previously reported the simultaneous presence of both low molecular weight and high molecular weight natriuretic substances in human urine. The low molecular weight substance produced an immediate but short-lived natriuresis. The high molecular weight substance produced a delayed but long-acting natriuresis. The results shown in FIG. 5 illustrate that both an early and sustained response in sodium excretion is observed in response to administration of the semi-purified 12 kD Na-K-ATPase inhibitor.

These results indicate that the semi-purified preparation containing the 12 kD compound and low molecular weight substances isolated from plasma induced natriuresis in an animal model with the characteristic response of the presence of both high and low molecular weight natriuretic substances. Therefore, these results, in combination with the results demonstrating separation of low molecular weight substances having Na-K-ATPase inhibitory and vasoconstrictive activity from the 12 kD compound (see infra) also suggest that low molecular weight Na-K-ATPase inhibiting substances separated from the 12 kD compound possess natriuretic activity.

EXAMPLE II

Separation of Low Molecular Weight Na-K-ATPase Inhibitors from the 12 kD Na-K-ATPase Inhibitor This example describes the isolation of low molecular weight natriuretic inhibitors from plasma.

Separation of low molecular weight (less than 500 daltons) inhibiting substances from the 12 kD compound was achieved by alkalinizing the filtrate obtained after treatment of the chilled, pre-filtered plasma with formic acid and mercaptoethanol and filtering to remove substances having a molecular weight greater than 30 kD. Alkalinization was accomplished using 0.8M NaOH to a pH of approximately 12. The alkalinized preparation was then applied to a reverse phase C18 HPLC column and eluted with a linear water/acetonitrile gradient from 0% to 100% acetonitrile (from 100% to 0% water) containing 0.1% TFA in each solvent as described above.

Figure 6:
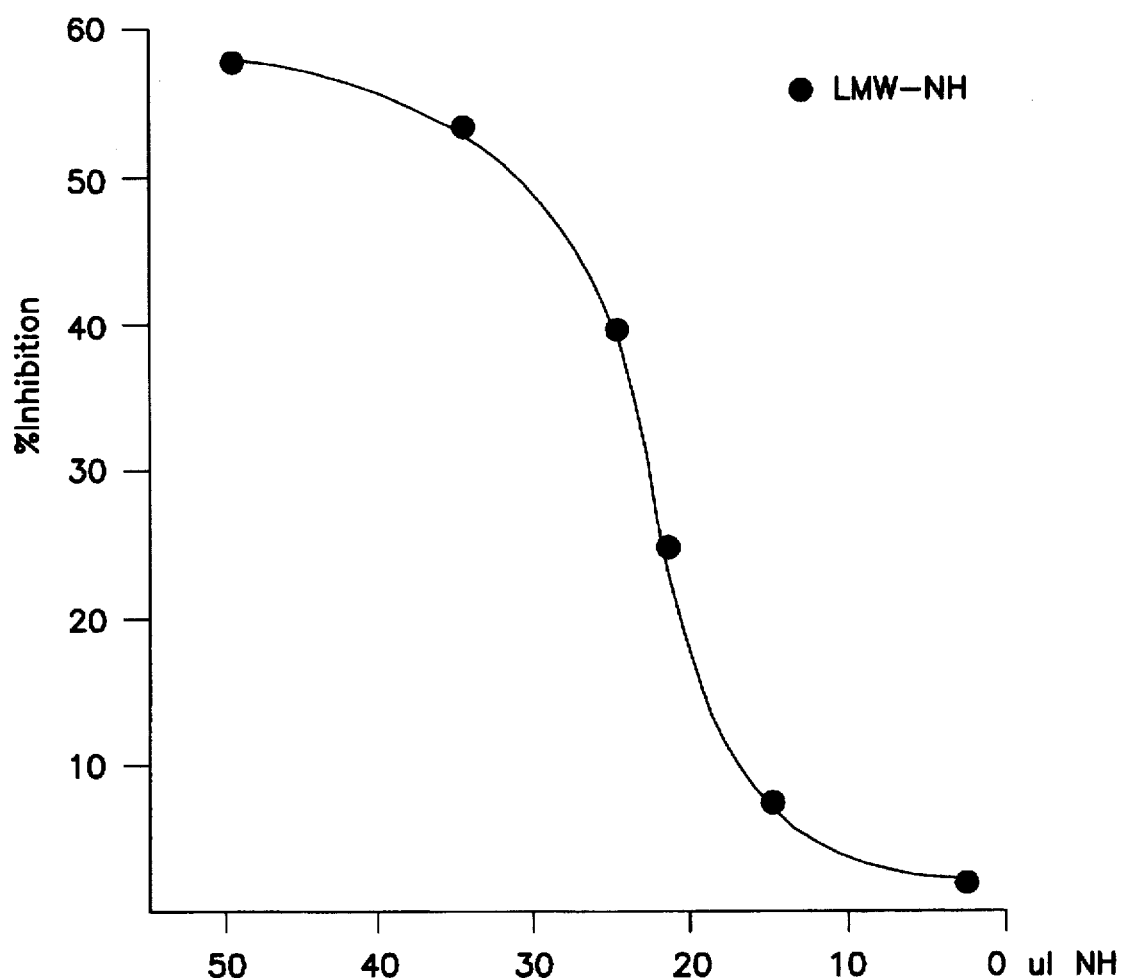
FIG. 6 is a graph of the Na-K-ATPase inhibition dose response curve for HPLC purified low molecular weight inhibitor, as described in Example II, infra.
Figure 7:
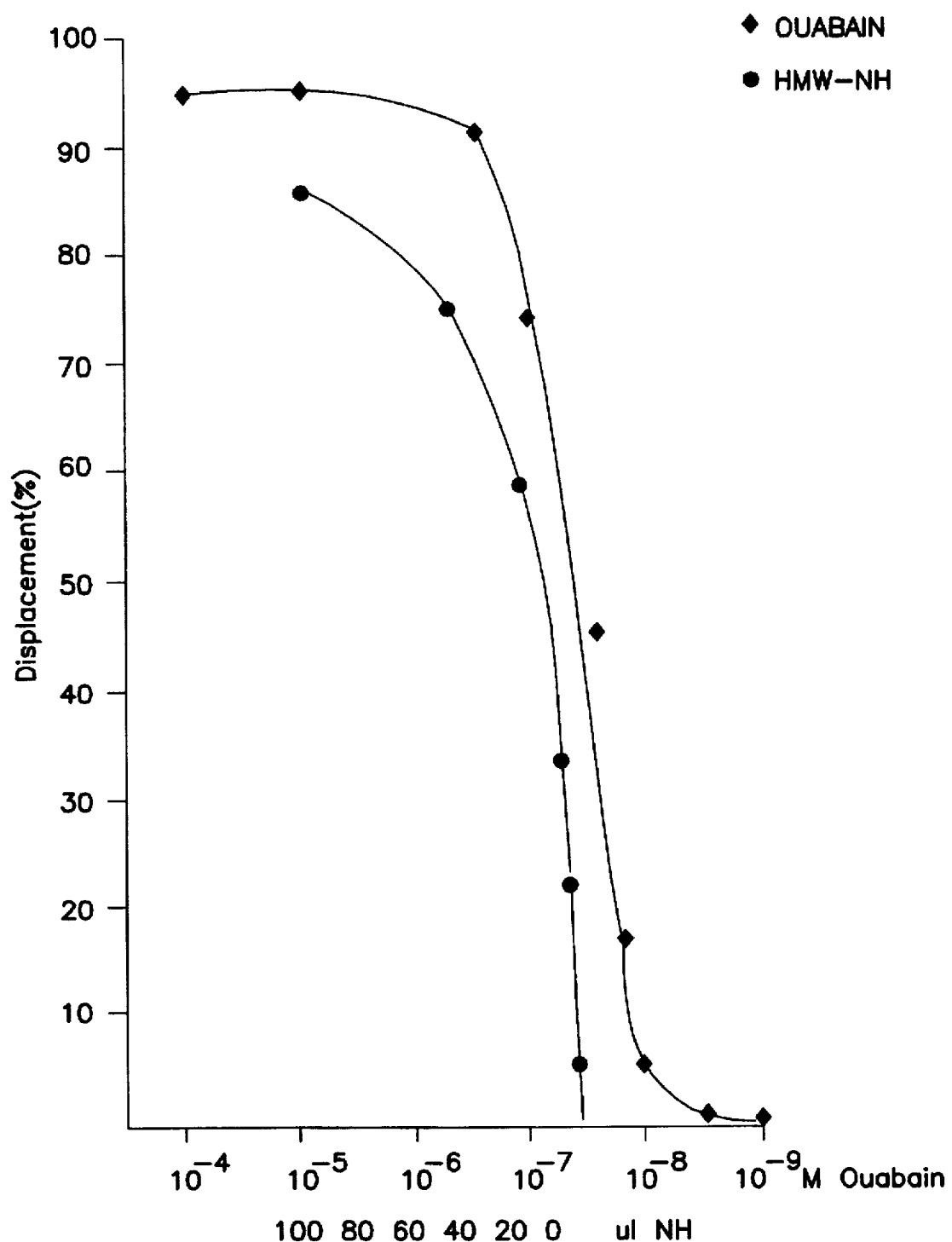
FIG. 7 is a graph of the $^3$H-ouabain displacement dose response curve for HPLC purified low molecular weight inhibitor, as described in Example II, infra.
Figure 8:
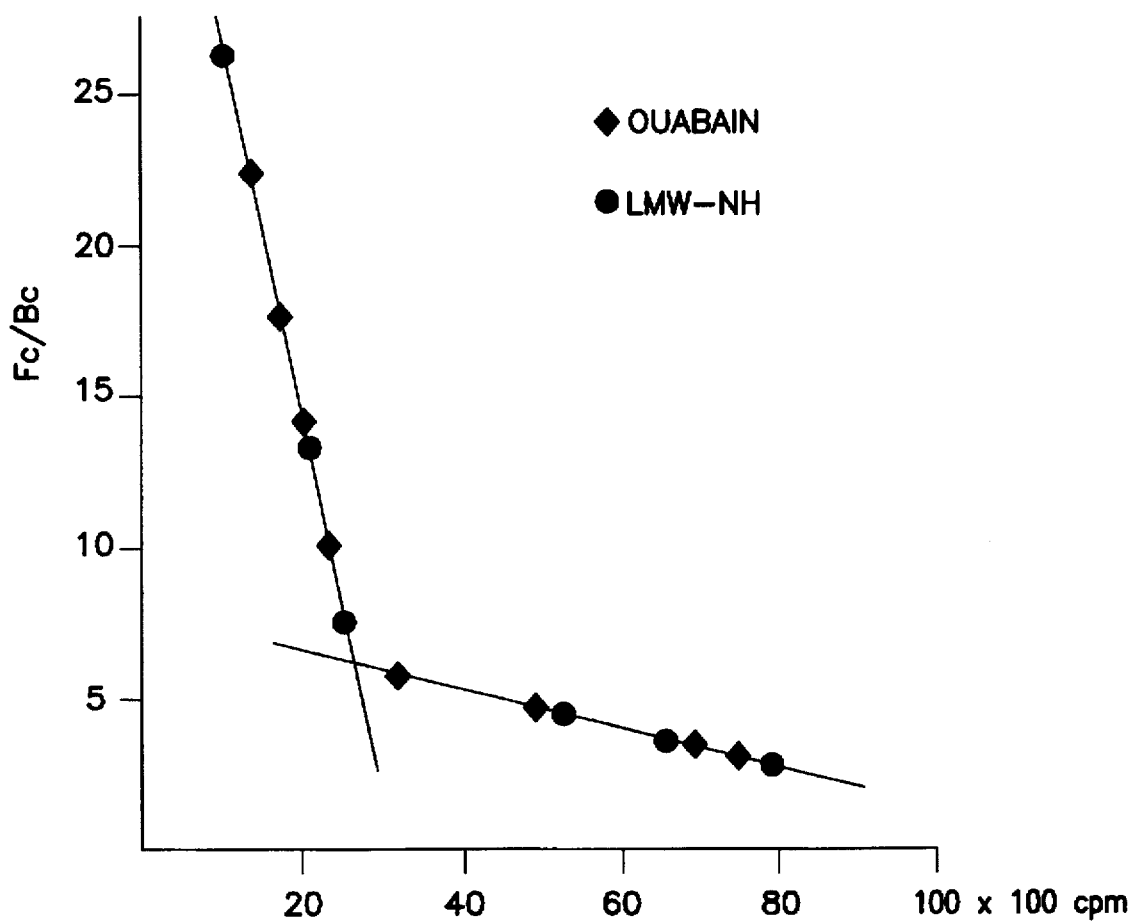
FIG. 8 is a Scatchard plot analysis of HPLC purified low molecular weight inhibitor compared to ouabain, as described in Example II, infra.

The active material (as subsequently determined by the Na-K-ATPase inhibition assay) eluted from the C18 column between 2–3 minutes when a flow rate of 2 ml/minute was employed. This active material, which was shown to have a molecular weight of less than 500 daltons by passage through a YC-05 Amicon® membrane, was then lyophilized and made up in distilled water, for subsequent testing of activity by Na-K-ATPase inhibition, (FIG. 6), $^3$H-ouabain displacement (FIG. 7) and Scatchard plot analysis (FIG. 8). As with the 12 kD inhibitor, a dose response curve was demonstrated for both assays and the inhibitor material was observed to bind to both high and low affinity receptors. These results confirmed that the low molecular weight Na-K-ATPase inhibitory substances possessed Na-K-ATPase inhibitory activity, and displaced ouabain.

Further Purification of Low Molecular Weight Inhibitor Substances by Electrochemical Detection Electrochemical detection was performed as described above. The active Na-K-ATPase inhibiting low molecular weight material obtained after elution from the C18 column by HPLC as described above was lyophilized and reconstituted in 1 ml of distilled water. Then 50 µl of this preparation was then injected onto a 25 cm reversed phase 3 micron high resolution C18 column using a Rheodyne (Alltech Assoc. Inc., Deerfield, Ill.) injection valve. The temperature of the column (55° C.) was maintained by an exterior heating jacket. The column was equilibrated with an elution buffer containing water, methanol, 0.1M phosphate buffer and an ion pairing agent. The Na-K-ATPase inhibitory compounds were eluted off the column using an isocratic gradient at a flowrate of 0.75 ml/min (similar results can be achieved with a flow rate ranging between 0.2 ml to 1.0 ml/min). The eluate was monitored electrochemically and the data were recorded with a chart recorder. The material of interest eluted after the solvent peaks and after void volume.

Figure 9:
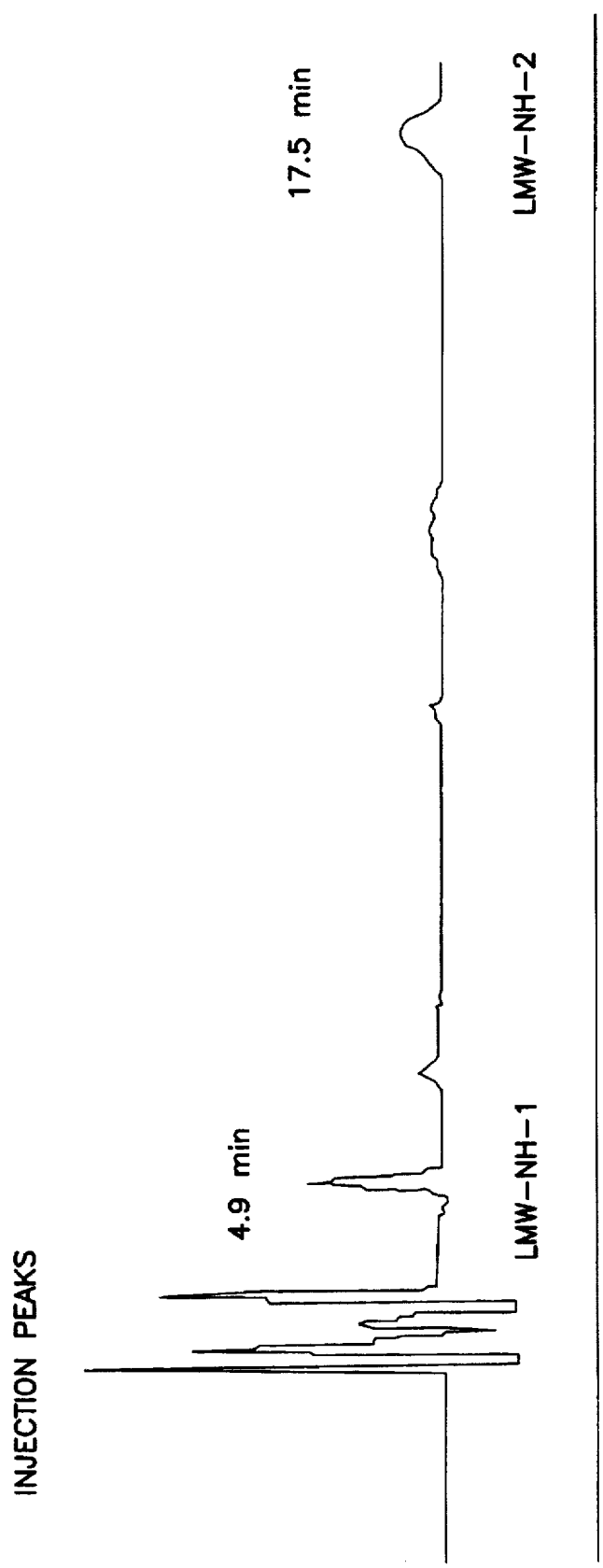
FIG. 9 depicts the elution profile of purified low molecular weight inhibitor analyzed by electrochemical detection, as described in Example II, infra.

At a flow rate of 0.75 ml/minute compounds having Na-K-ATPase inhibitory activity (as determined by the Na-K-ATPase inhibitory assay described infra) were recovered in two fractions at 4.9 minutes ("first" low molecular weight compound) and 17.5 minutes ("second" low molecular weight compound) (see FIG. 9). These fractions were collected separately into pre-washed, clean vials.

Desalting of each fraction obtained from the 3µ HPLC column to remove phosphate ions was achieved using SEP PAK® chromatography cartridges, purchased from Waters Associates (Milford, Mass.). Prior to the application to the cartridges, the pH of each fraction was adjusted to pH 10 to pH 13 to cause the low molecular weight compounds to bind to the cartridges and to prevent interference from the elution solvents with the assay for ATPase inhibition. The cartridges were activated by passing 2×5 ml of 100% methanol through the cartridge followed by 4 washings using 5 ml of distilled water. The samples were then applied to the cartridges and subsequently washed four times with 10 ml of distilled water to remove all salts.

The material contained in the first fraction eluting at 4.9 minutes from the ECD column was eluted from the SEP PAK® cartridge first with 100% distilled water/0% acetonitrile/0.1% TFA. Then a second elution was performed using 80% distilled water/20% acetonitrile/0.1%

TFA. The material contained in the second fraction eluting at 17.5 minutes from the ECD column was eluted from the cartridge first with 100% distilled water/0% acetonitrile/0.1% TFA, then with 80% water/20 acetonitrile/0.1% TFA. All fractions were then lyophilized and subsequently assayed for Na-K-ATPase inhibitory activity.

The 4.9 minute material was recovered in the 100% water/0% acetonitrile/0.1% TFA. This fraction exhibited Na-K-ATPase inhibitory activity. No Na-K-ATPase inhibitory activity was recovered from the second elution of this material. The 17.5 minute material was recovered in the 80% water/20% acetonitrile/0.1% TFA. No Na-K-ATPase inhibitory activity was recovered from the elution using 100% water/0% acetonitrile/0.1% TFA.

Structural Analysis of Low Molecular Weight Inhibitor

FAB Mass spectra were obtained as described by Tamura et al., supra, with modifications as follows. A TSQ/70 Triplequadropol mass spectrometer equipped with a high-field magnet and a PDP 1173 data system was used. The fast atom bombardment gun was of a cesium ion gun type and was operated at 10 V. The mass spectrometer was adjusted at an accelerating voltage of 10 V. Scans were obtained at 390 AMU(atomic mass units)/s. The purified samples were reconstituted in distilled water (1–2 µl) and were introduced onto a stainless-steel target with a thin film of neat glycerol as a matrix.

Figure 10A:
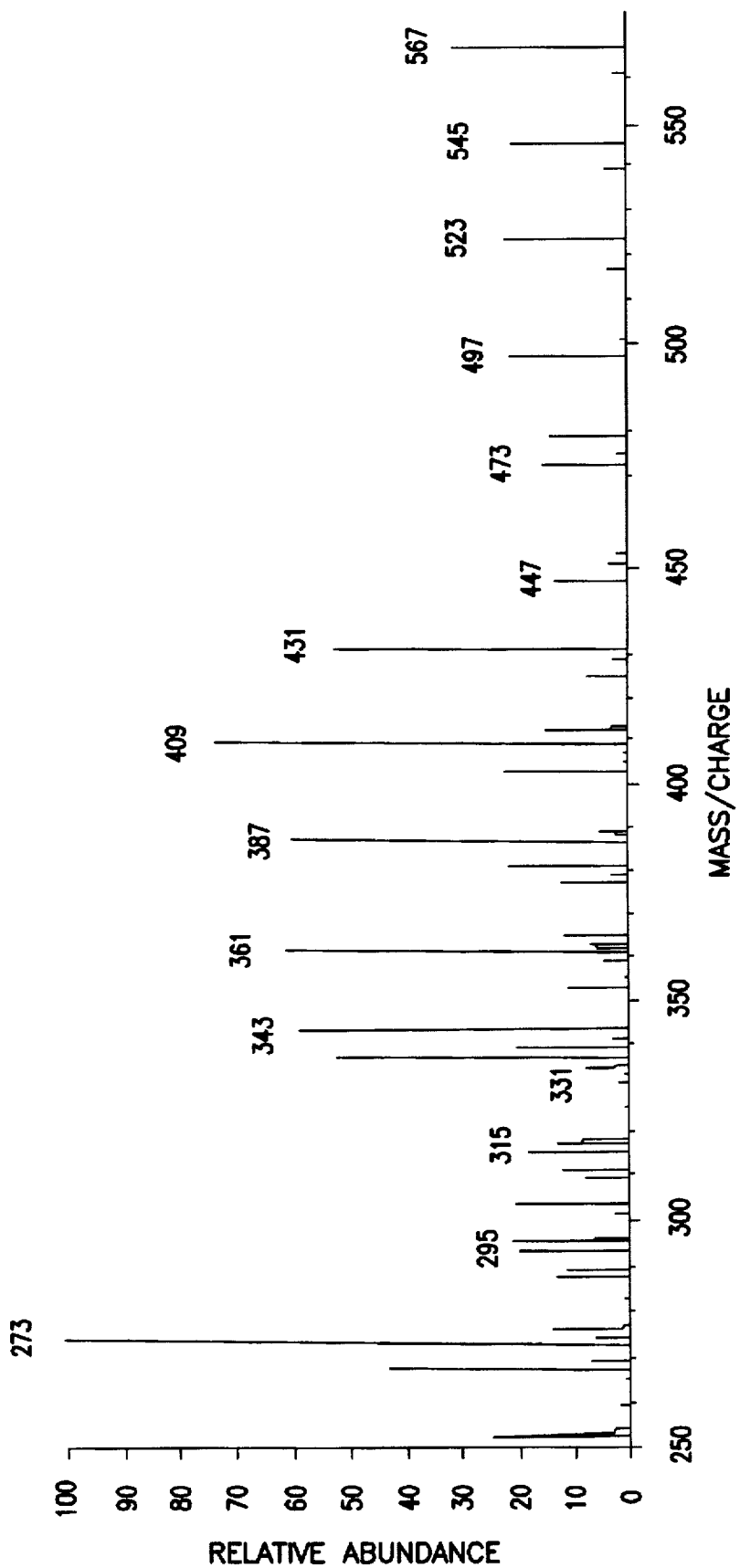
FIG. 10 depicts mass spectroscopy analysis of purified low molecular weight inhibitor (first peak detected electrochemically at a retention time of 4.9 min), as described in Example II, infra.
Figure 10B:
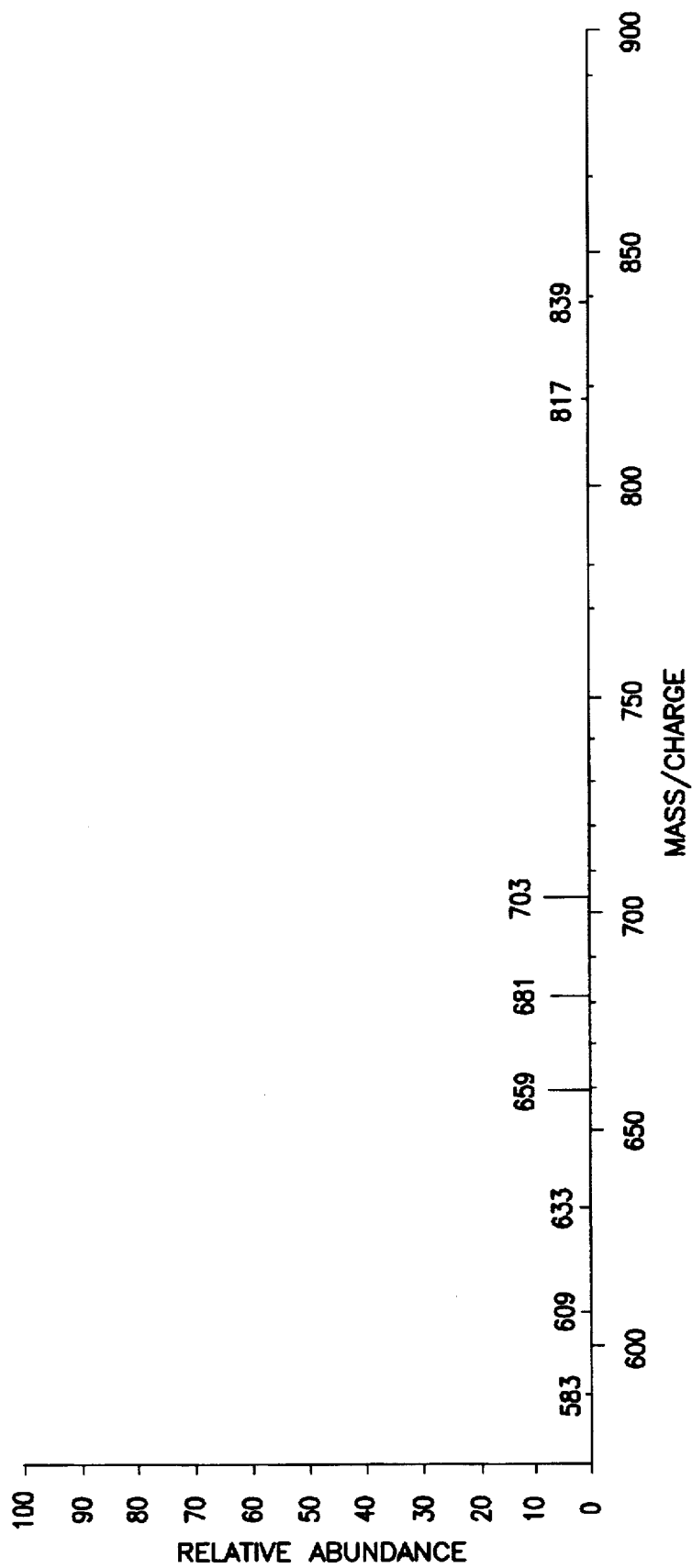

FAB Mass spectroscopy analysis of the purified, isolated first peak revealed a pattern consistent with a single Na-K-ATPase inhibiting compound of molecular weight of 408 daltons (FIG. 10). FIG. 10 confirms that the low molecular weight compound of interest has a molecular weight of 408 daltons: the spectrum indicates a peak at 409 daltons molecular weight containing the 408 dalton substance plus hydrogen; a peak at 431 daltons which contains the 408 dalton substance plus sodium; a peak at 447 daltons which contains the 408 dalton substance plus potassium and a peak at 817 daltons which contains a dimer (2×408 daltons plus hydrogen).

EXAMPLE III

Effects of Low Molecular Weight Na-K-ATPAse Inhibitors on Vasoconstriction

This example demonstrates the effect of the low molecular weight substances, isolated as described in Example I, on vascular reactivity.

The low molecular weight preparation initially separated from the 12 kD compound by HPLC containing both low molecular weight substances (prior to ECD) was tested in a vasoconstrictor assay (Weber et al., *Am. J. Hypertens.*, supra) employing rabbit femoral arteries bathed in Krebs-bicarbonate solution. Viability of the preparation was confirmed by testing contractility of the arteries after exposure to 60 mmol potassium. After confirmation of contractility, fresh Krebs-bicarbonate bath was prepared and the low molecular weight Na-K-ATPase inhibitors in a concentration corresponding to $12 \times 10^{-6}$M ouabain-equivalents (as determined by the Na-K-ATPase assay described above) were added to the bath. This produced vasoconstriction equivalent to $3 \times 10^{-9}$M norepinephrine or $3 \times 10^{-10}$M angiotensin II. The vasoconstriction was reversed by addition of $10^{-5}$M nifedipine (Sigma Chemical Co., St. Louis, Mass.), a calcium channel blocker.

Figure 14A:
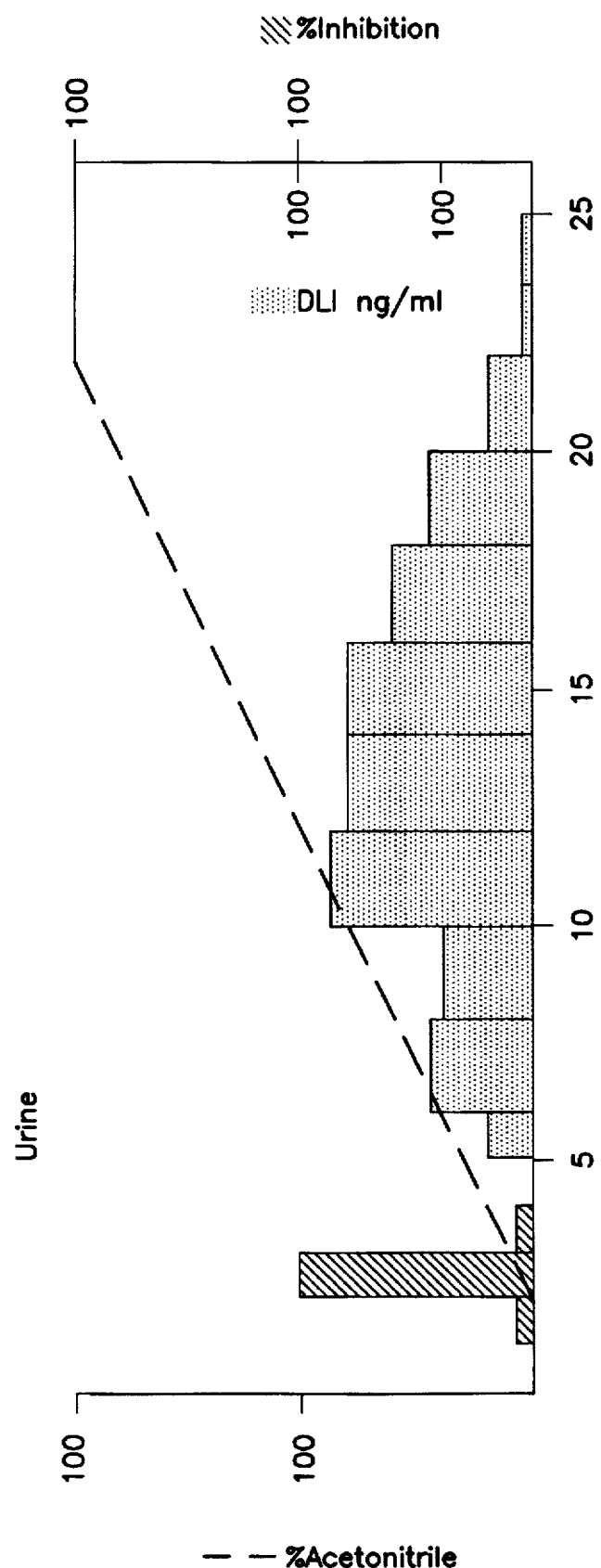
FIG. 14 is a comparison of the HPLC elution profile of low molecular weight Na-K-ATPase inhibiting substances and digoxin-like immunoreactivity in plasma and urine following HPLC as described in Example IV, infra.
Figure 14B:
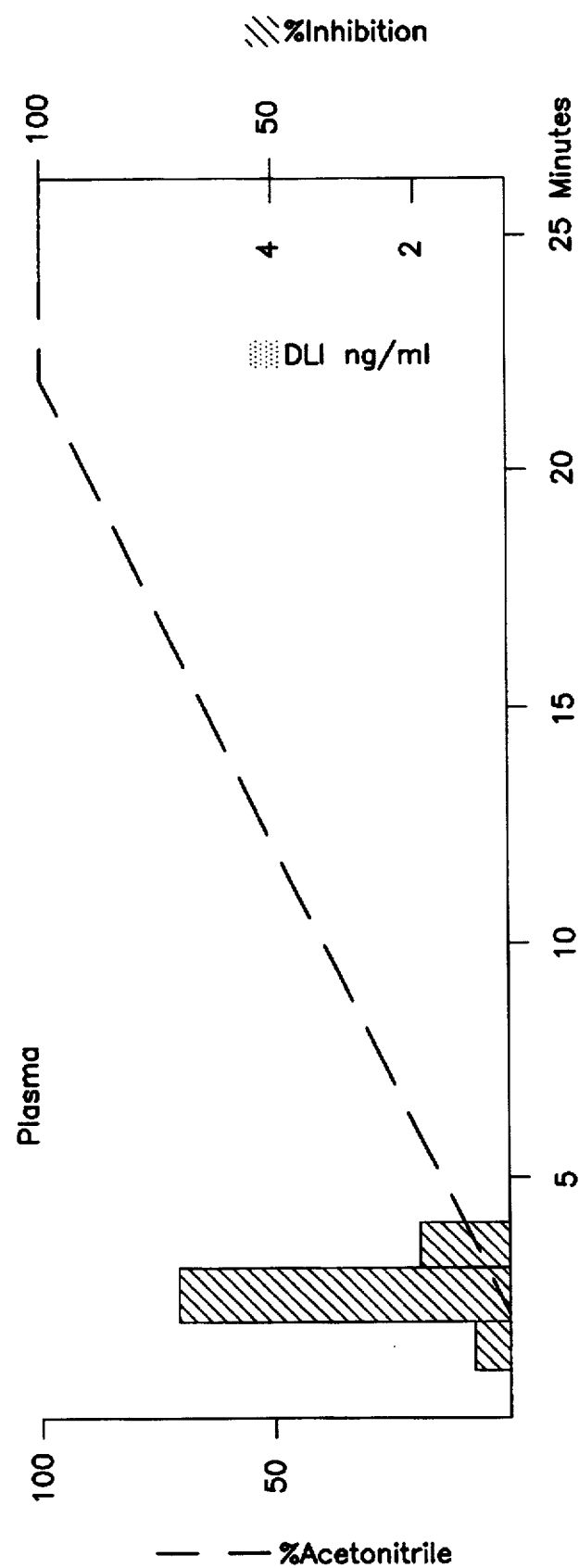

It has been shown that a low molecular weight urinary Na-K-ATPase inhibitor, with elution characteristics similar to the 408 dalton plasma Na-K-ATPase inhibitor described herein, had intrinsic vasoconstrictor properties, enhanced the vasoconstriction produced by norepinephrine and angiotensin II, and its vasoconstrictor effect could be prevented by removal of calcium ions from bathing solution (Weber et al., supra). Thus, the 408 dalton plasma Na-K-ATPase inhibitor of this invention may be the same or similar as the previously isolated urinary inhibitor as further indicated by the identical elution characteristics on HPLC (FIG. 14, infra).

Examples I and II demonstrate that the predominant circulating natriuretic, Na-K-ATPase transport inhibitor obtained from hypertensive and primary aldosteronism plasma is a 12 kD compound associated with low molecular weight (less than 500 dalton) inhibitor substances. The 12 kD compound is released from higher molecular weight binding proteins by treatment with formic acid and mercaptoethanol and exhibits natriuretic, Na-K-ATPase inhibitory, and $^3$H-ouabain displacement characteristics and binds to both high and low affinity binding sites on purified Na-K-ATPase. When the 12 kD compound is alkalinized and further purified using reverse phase C18 HPLC, two low molecular weight fractions (containing compounds of less than 500 daltons molecular weight) are recovered, both of which also inhibit Na-K-ATPase. The preparation containing both low molecular weight inhibitory substances also displaces $^3$H-ouabain and binds to both high and low affinity binding sites and cause vasoconstriction which is abolished by calcium channel blockers but does not demonstrate digoxin-like immunoreactivity.

EXAMPLE III

Presence of Urinary Na-K-ATPase Inhibitors and Digoxin-Like Immunoreactive substances in Acute Congestive Heart Failure Thirteen patients (aged 48–84) were admitted to the Coronary Care Unit at Cedars-Sinai Medical Center (Los Angeles, Calif.) with a diagnosis of acute congestive heart failure (CHF). The diagnosis of CHF was based on clinical symptoms of acute onset of dyspnea along with physical and radiological findings of pulmonary congestion or edema. In 9 patients, in addition to their clinical variables, elevated pulmonary capillary wedge pressure >20 mm Hg during right heart catherization and/or depressed left ventricular ejection fraction <40% (on radionucleotide ventriculargraphy or 2 dimension echo) were documented during hospitalization of patients confirming the presence of impaired cardiac output. Patients were later divided into group I (4 patients) and group II (9 patients) according to levels of urinary Na-K-ATPase inhibitors subsequently determined. Group I demonstrated elevated levels of the earlier eluting of two urinary inhibitors whereas group II demonstrated diminished levels of this inhibitor. Measurements of urinary digoxin-like immunoreactive substances were obtained in five patients who were not taking therapeutic digitalis preparations.

24 hour urine collections were obtained on all patients, in most cases beginning with the day of admission or the following day. A second 24 hour urine was obtained after the patient had shown response to treatment. Treatment consisted primarily of diuretics and vasodilators (hydralazine, nitroglycerine, angiotensin converting enzyme inhibitors). For comparison, 24 hour urine collection was also obtained from 9 normotensive control subjects without heart failure, aged 25–60 and from 10 hypertensive patients not in CHF, aged 41–65.

Separation of Urinary Na-K-ATPase Inhibitors 50 ml urine samples were lyophilized, reconstituted in distilled water and then separated on Sephadex G-25 columns (45 cm×2.5 cm) employing 10 mM ammonium acetate, pH 7.0 as eluent. The salt fraction and post-salt fraction were pooled and subsequently absorbed onto a SEP PAK® cartridge to remove interfering substances such as calcium, phosphorus, etc., by washing the cartridge repeatedly with distilled water. A stepwise acetonitrile (ACN)/ 0.1% TFA gradient was used to separate out the Na-K-ATPase inhibitors and compounds cross-reacting with digoxin antibody. Na-K-ATPase inhibitory activity eluted in 20% ACN/0.1% TFA and 50% ACN/0.1% TFA. Each fraction was lyophilized and then tested for both Na-K-ATPase inhibitory activity (uNKAI) and digoxin-like immunoreactivity (DLI). Na-K-ATPase activity was expressed as moles ouabain equivalents (Oeq.)/24 hour urine, whereas DLI was expressed as ng digoxin equivalents (Deq.)/24 hour urine. As the majority of DLI was found in the 50% ACN/0.1% TFA fraction, the immunoreactivity results in the 20% ACN/0.1% TFA and in 50% ACN/0.1% TFA fractions were combined.

Measurement of Na-K-ATPase inhibitors and digoxin-like immunoreactivity was not affected by the presence of exogenous digoxin, because with Sephadex G-25 separation of urine radiolabeled digoxin elutes prior to the salt fraction.

The Na-K-ATPase inhibition assay and digoxin radioimmunoassays were performed as described above. Concentration of the digoxin-like immunoreactivity is expressed as Deq. and was read from a digoxin standard curve with standards ranging from 0 to 4 ng/ml.

Figure 11:
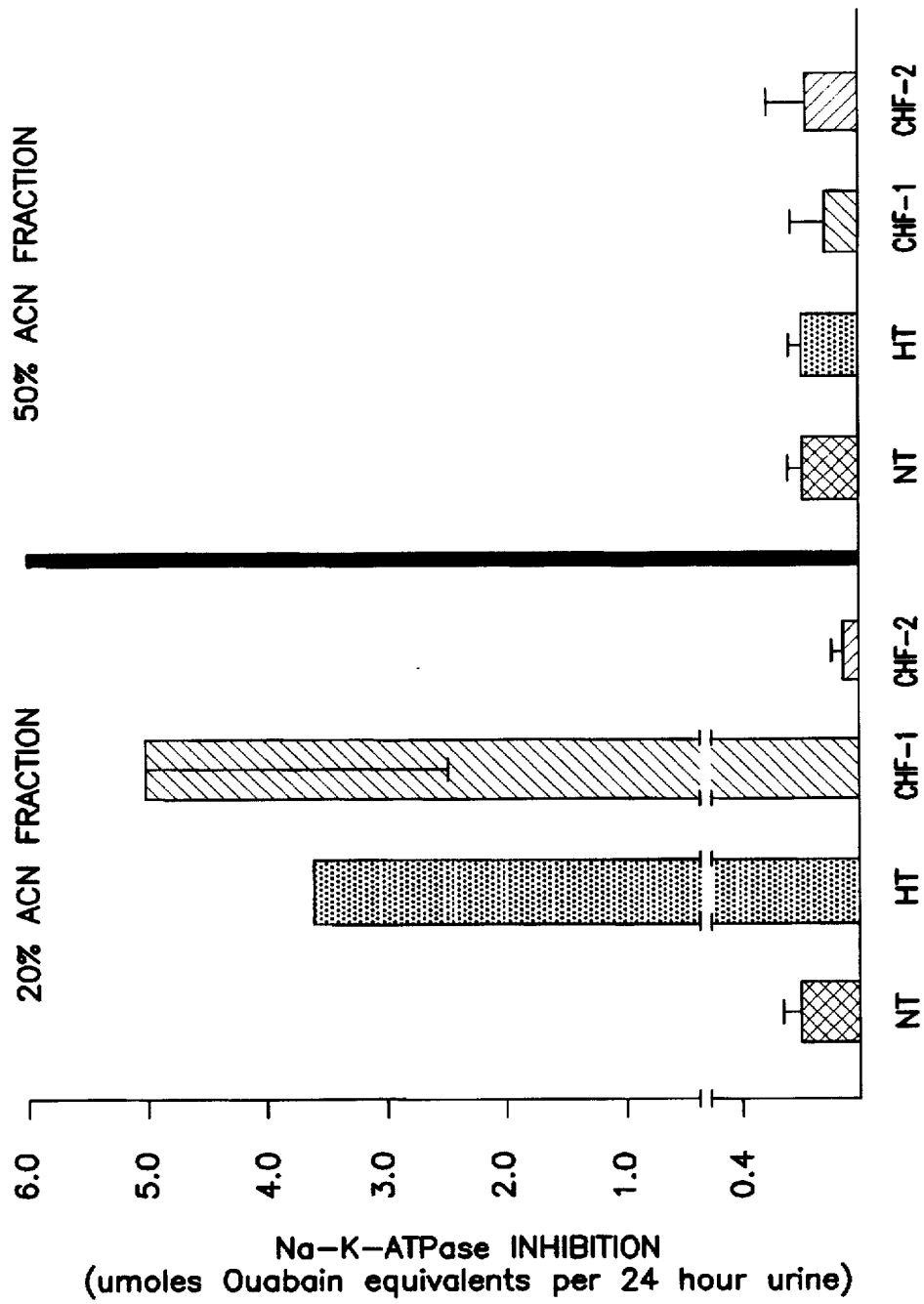
FIG. 11 depicts the concentration of two urinary low molecular weight Na-K-ATPase inhibitors (uNKAI) from patients with congestive heart failure, hypertension and normal controls, as described in Example III, infra (NT=Normotensive; HT=Hypertensive; CHF-1=Congestive heart failure, group I; CHF-2=Congestive heart failure, group II).

As shown in FIG. 11, group I and group II CHF patients, hypertensive patients and normal controls demonstrated equal amounts of a low molecular weight urinary Na-K-ATPase inhibitor eluting in the 50% ACN/0.1% TFA fraction, with an inhibitor concentration ranging between 0.12±0.12 and 0.2±0.1 μmoles Oeq./24 hour urine. On the other hand, Na-K-ATPase inhibitory material, eluting in the 20% ACN/0.1% TFA fraction exhibited significant differences among the groups. In the normotensive group, the mean value for this uNKAI was 0.20±0.05 μmoles Oeq./24 hour urine. Significantly increased levels of uNKAI were measured in hypertension (averaging 3.63±0.81 μmoles Oeq./24 hour urine) and in CHF group I (5.0±2.6 μmoles Oeq./24 hour urine). CHF group II demonstrated significantly decreased levels of uNKAI, averaging 0.06±0.004 μmoles Oeq./24 hour urine (p<0.001 compared to normal controls).

Measurement of urinary digoxin-like immunoreactive activity revealed, as demonstrated in FIG. 11, significant differences among all groups. The highest concentration of DLI was detectable in patients with CHF (589.5±144 ng Deq./24 hour urine). Normotensives (168±24 ng Deq./24 hour urine) and hypertensives (77±14 ng Deq./24 hour urine) both exhibited lower levels (p<0.001) of DLI compared to CHF patients.

Figure 12:
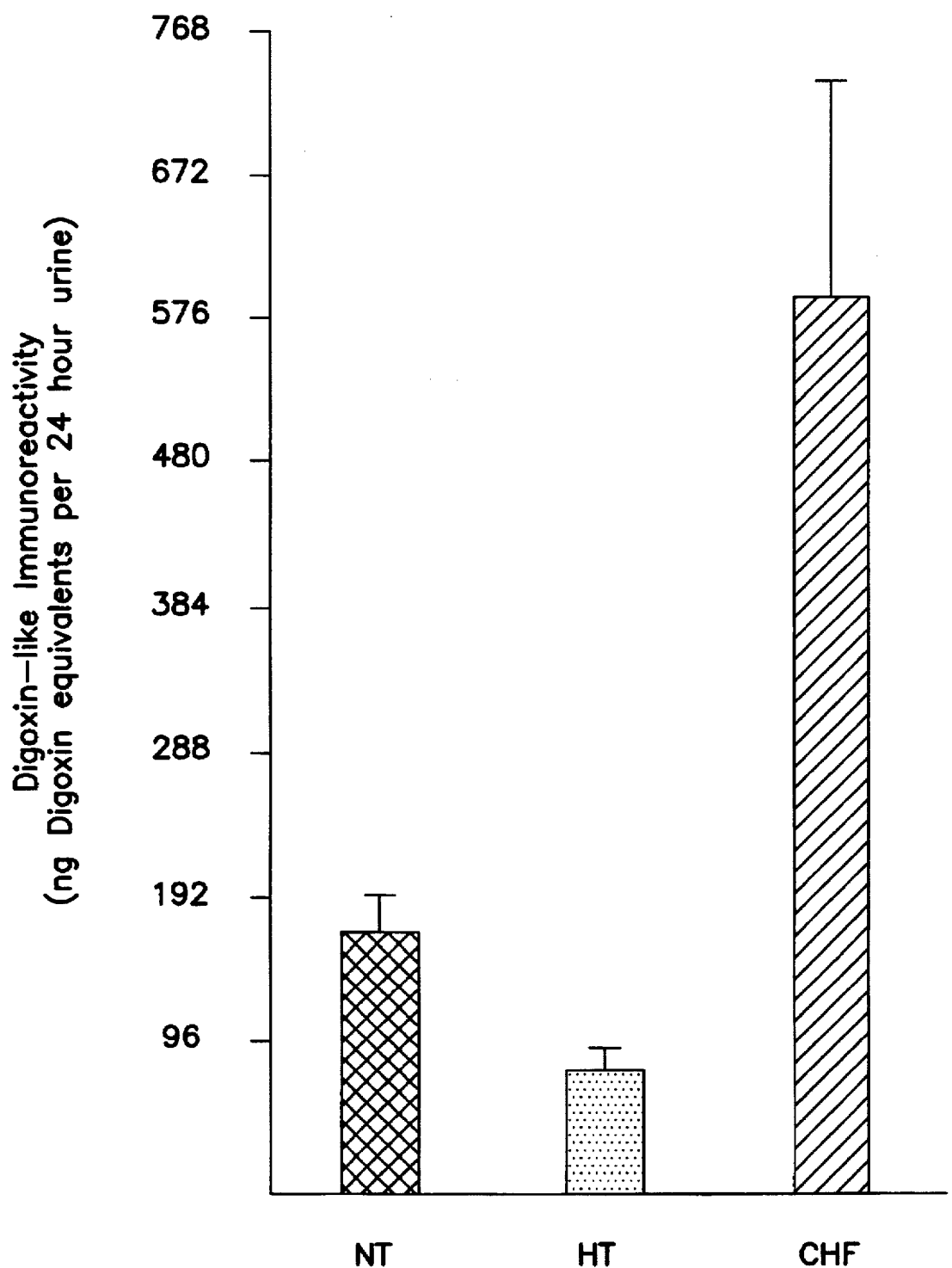
FIG. 12 depicts the results of measurement of urinary digoxin-like immunoreactivity from patients with congestive heart failure, hypertension and normal controls, as described in Example III, infra (NT=Normotensive; HT=Hypertensive; CHF=Congestive heart failure).
Figure 13:
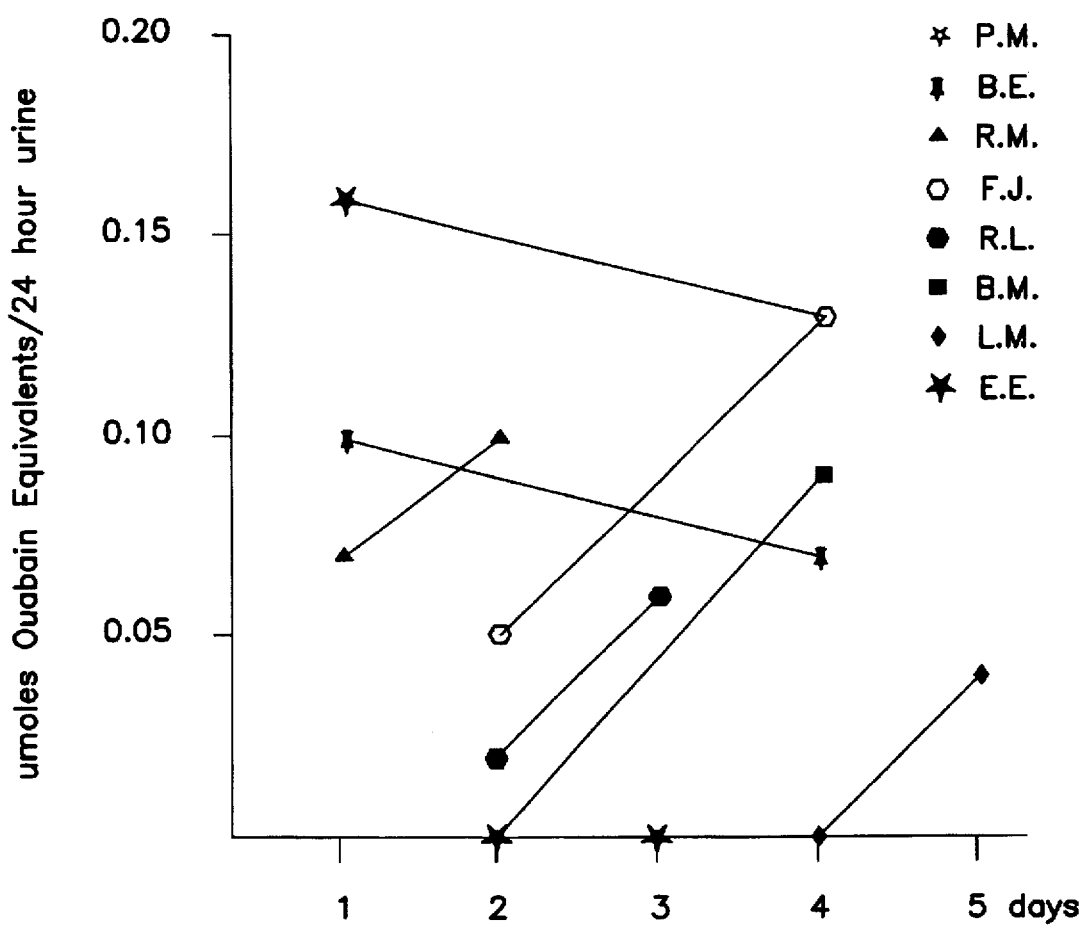
FIG. 13 is a graph showing increases in low molecular weight urinary Na-K-ATPase inhibitor (uNKAI) during treatment of congestive heart failure in group II patients, as described in Example III, infra.

Increases in uNKAI following treatment of CHF were observed in the majority of patients in Group II as seen by the sequential changes in the excretion of the 20% ACN/ 0.1% TFA uNKAI plotted in FIG. 12.

These results further support the conclusion that patients with CHF have a deficiency of a natriuretic, transport inhibiting substance (here measured as an urinary Na-K-ATPase inhibitor) manifested in this example by a decreased level of the earlier eluting of two low molecular weight urinary Na-K-ATPase inhibitors. This was seen in 9 out of 13 patients studied; in the majority of these patients the urinary Na-K-ATPase inhibitor increased following treatment of CHF. In contrast, measurements of urinary digoxin-like immunoreactivity revealed an increase in this material in CHF as compared to both hypertensives and normotensive controls. This is consistent with the previously reported observations of discrepancies between measurements of Na-K-ATPase inhibition and digoxin cross-reactivity as assays for natriuretic hormone in urine and plasma. This implies the presence of more than one digitalis-like substance with differing properties. This suggests that there may be an endogenous digitalis-like substance which, unlike the low molecular weight natriuretic hormone described herein, increases in a compensatory manner in congestive heart failure.

In this example, 9 out of 13 patients admitted with a diagnosis of acute CHF demonstrated a reduced excretion of the earlier eluting of two low molecular weight urinary Na-K-ATPase inhibitors. Diminished clearing by the kidneys is not an explanation for these data because the activity of the urinary inhibitor was not related to the level of renal function. Of the four patients not demonstrating low levels of the urinary inhibitor, one had an unconfirmed diagnosis of CHF and in the other heart failure resolved prior to initiation of the urine collection. The higher than normal urinary Na-K-ATPase inhibitory activity in Group I patients may be a result of the presence of hypertension in two of the patients, and/or by the fact that the CHF patients were older as a group.

EXAMPLE IV

Comparison of Substances Isolated by HPLC from Urine and Plasma

A comparison was done of low molecular weight Na-K-ATPase inhibitory substances and digoxin-like immunoreactivity from human plasma and urine eluted by HPLC on a C18 column. Samples of urine and plasma were from hypertensive subjects. Procedures used for separation of low molecular weight substances from each type of sample were as described in Example I, supra, except that urine samples were not treated with formic acid and mercaptoethanol and were not alkalinized. The results of HPLC analysis are shown in FIG. 14.

As can be seen in FIG. 14, the low molecular weight substances obtained used the procedures described herein eluted in the same fraction from the HPLC column for urine and plasma. These results suggest that these substances may be related or are the compound. This provides additional support for the use of the low molecular weight Na-K-ATPase inhibiting substance isolated from plasma and having natriuretic properties described herein for the treatment of diseases associated with increased amounts of natriuretic substances, such as hypertension, as well as conditions such as CHF where a deficiency of natriuretic substances may be related to the pathology of the disease.

While we have presented particular embodiments of the invention herein, it is apparent that variations and modifications can be effected within the scope of the invention. Therefore, it will be appreciated that the scope of this invention is to be defined by the claims appended hereto rather than by the specific embodiments that have been presented herein by way of example.

We claim:

1. A substantially pure isolated low molecular weight plasma inhibitor of Na-K-ATPase occurring in human plasma and characterized by having vasoconstrictive and natriuretic activity and displacing ouabain from its receptor and lacking reactivity with anti-digoxin antibody, said inhibitor having a molecular weight of less than 500 peptide.

* * * * *